(12) United States Patent
Carrillo Gonzalez et al.

(10) Patent No.: US 11,458,035 B2
(45) Date of Patent: Oct. 4, 2022

(54) DENTAL APPLIANCE TO REDUCE SNORING

(71) Applicants: Roberto Carrillo Gonzalez, San Pedro Garza Garcia (MX); Roberto Carrillo Fuentevilla, San Pedro Garza Garcia (MX)

(72) Inventors: Roberto Carrillo Gonzalez, San Pedro Garza Garcia (MX); Roberto Carrillo Fuentevilla, San Pedro Garza Garcia (MX)

( * ) Notice: Subject to any disclaimer, the term of this patent is extended or adjusted under 35 U.S.C. 154(b) by 639 days.

(21) Appl. No.: 15/838,349

(22) Filed: Dec. 11, 2017

(65) Prior Publication Data
US 2018/0161195 A1    Jun. 14, 2018

Related U.S. Application Data

(60) Provisional application No. 62/432,555, filed on Dec. 9, 2016.

(51) Int. Cl.
    *A61F 5/56* (2006.01)
(52) U.S. Cl.
    CPC .................................. *A61F 5/566* (2013.01)
(58) Field of Classification Search
    CPC ...... A61F 5/56; A61F 5/566; A61F 2005/563; A61C 7/08
    USPC ........................................................... 433/6
    See application file for complete search history.

(56) References Cited

U.S. PATENT DOCUMENTS

| 5,120,218 | A | * | 6/1992 | Hanson | A61C 7/36 |
| | | | | | 433/19 |
| 5,584,687 | A | * | 12/1996 | Sullivan | A61F 5/566 |
| | | | | | 128/861 |
| 5,645,423 | A | * | 7/1997 | Collins, Jr. | A61C 7/36 |
| | | | | | 433/18 |
| 6,273,713 | B1 | * | 8/2001 | Liou | A61C 7/36 |
| | | | | | 433/19 |
| 8,047,845 | B2 | * | 11/2011 | Van Der Kerken | A61C 13/28 |
| | | | | | 433/179 |
| 2014/0230829 | A1 | * | 8/2014 | Rogers | A61F 5/566 |
| | | | | | 128/848 |

* cited by examiner

*Primary Examiner* — Rachael E Bredefeld
*Assistant Examiner* — Brant T Bennett
(74) *Attorney, Agent, or Firm* — Ferguson Braswell Fraser Kubasta PC

(57) ABSTRACT

In various implementations, a dental appliance may be utilized to increase an airway and/or reduce snoring. The dental appliance may include an adjustment member, sheath, and a connector that couples the adjustment member and the sheath. The adjustment member may be coupled to a first bite plate, which is positionable over at least a portion of a user's upper teeth. The sheath may be coupled to a second bite plate, which is positionable over at least a portion of a user's lower teeth. The dental appliance may push a user's mandible forward (e.g., closer to an anterior side of a user when compared to an initial position of the mandible) during use.

18 Claims, 23 Drawing Sheets

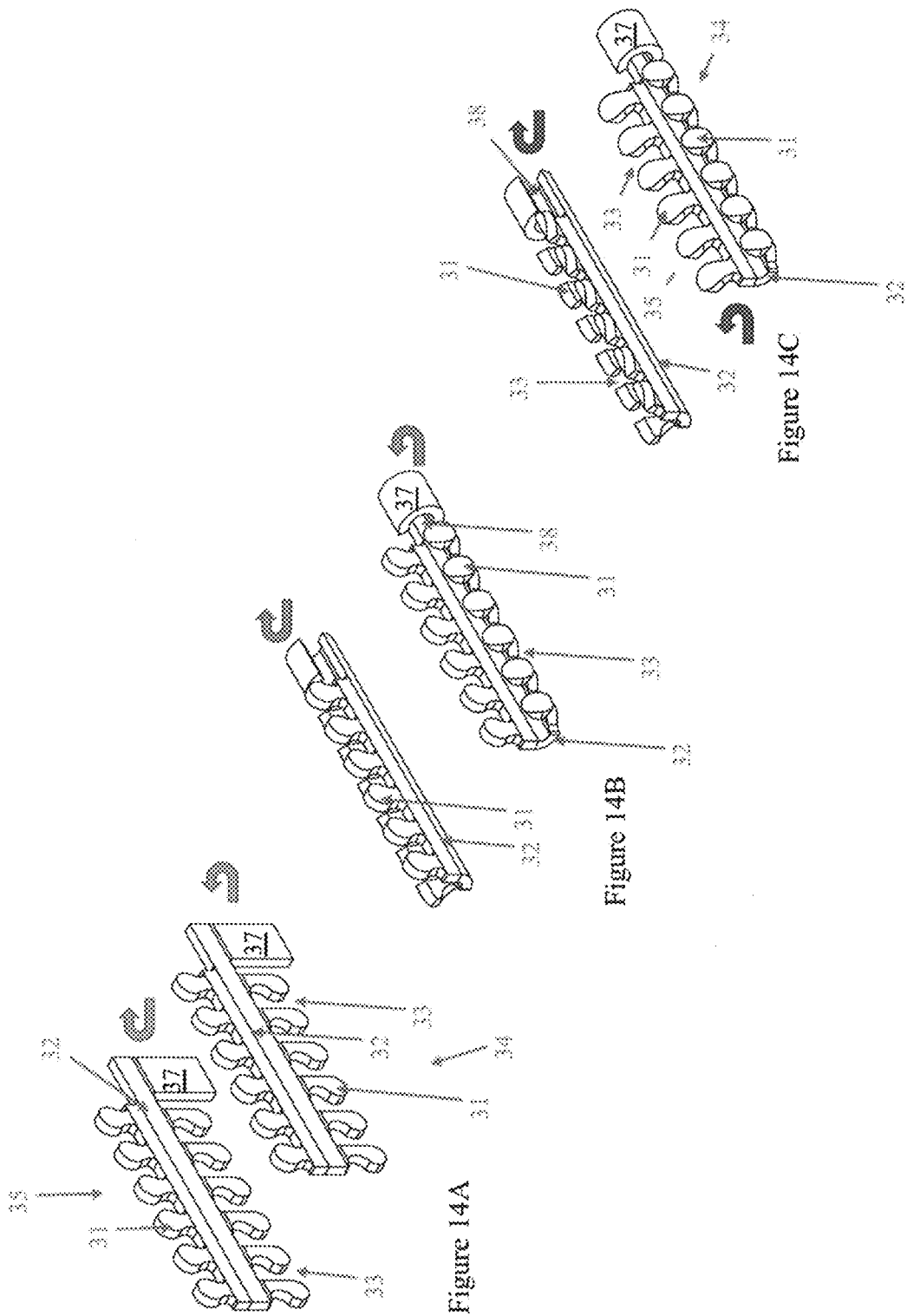

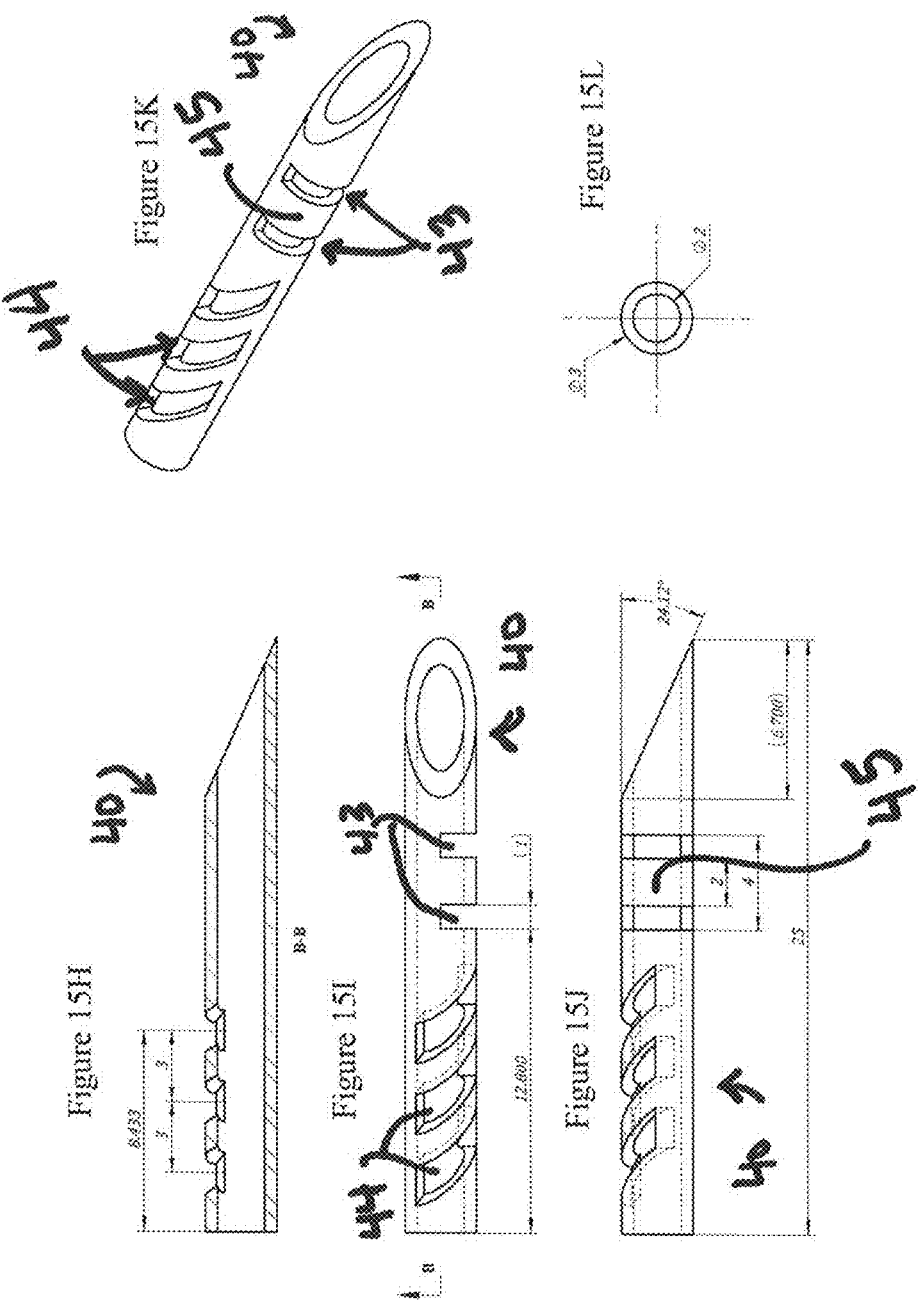

DENTAL APPLIANCE TO REDUCE SNORING

CROSS-REFERENCE TO RELATED APPLICATIONS

This application claims the benefit of priority to U.S. Provisional Patent Application No. 62/432,555, filed on Dec. 9, 2016 and entitled "Dental Appliance to Reduce Snoring", which is hereby incorporated by reference for all purposes.

TECHNICAL FIELD

The present invention relates to a dental appliance.

BACKGROUND

Snoring is a common sleep problem that may interfere with a person's sleep, a person's air intake, and/or other's sleeping in the proximity. Once a person's sleep is disrupted, the person may have trouble returning to sleep and/or be drowsy during the day. Some studies have even linked the vibrations caused by a person's snoring to increased risks of stroke and cardiac diseases. However, common anti-snoring devices are bulky and loud, such as CPAP (continuous positive airway pressure) machines.

SUMMARY

In various implementations, a dental appliance may be provided. The dental appliance may increase airways (e.g., increase area in the mouth through which air can flow) and thus decrease snoring and/or improve sleep. The dental appliance may move a user's mandible forward (e.g. towards an anterior side of a user) to increase the size of an airway in the user. Movement of the mandible forward and/or increasing the size of an airway in the user may decrease snoring.

The dental appliance may include at least two bite plates that are coupled via a connector. A first bit plate may be positioned on at least a portion of upper teeth (e.g., teeth in the maxilla) and the second bite plate may be positioned on at least a portion of the lower teeth (e.g., teeth in the mandible). The first bite plate may include a first adjustment member disposed on, for example, a facial side of the first bite plate. The first adjustment member may include protrusions. The second bite plate may include a sheath disposed, for example, on a facial side of the second bite plate. A connector may couple to the first bite plate via the adjustment member and the second bite plate via the sheath. A connector may couple to the bite plates proximate the facial sides of the bite plates to increase user comfort while wearing the device (e.g., by inhibiting displacement of the tongue from its natural position). The connector may be at least partially flexible to allow a user, in which the dental appliance is disposed, to move the user's mandible laterally and/or longitudinally (e.g., by the application of force in the direction of movement). The connector may be configured to move the mandible forward (e.g., towards an anterior side of the user) relative to the mandible's initial position in relation to the maxilla.

In some implementations, the connector may include two arms extending from a spring mechanism. A first arm may include a locking member, such as a curved portion, that can couple with the adjustment member of the first bite plate. The second arm may be disposed at least partially in the sheath. The spring mechanism may include one or more loops.

In some implementations, the dental appliance may include an attachment member and a sheath coupled via connector. The attachment member may be coupled to one or more upper teeth directly or indirectly. The sheath may be coupled to one or more upper teeth directly or indirectly. For example the attachment member and/or sheath may be coupled to teeth via bite plates, orthodontic bases, and/or orthodontic brackets.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 14A illustrates an implementation of an example adjustment member in an initial fabrication position.

FIG. 14B illustrates an implementation of an example adjustment member in a second fabrication position.

FIG. 14C illustrates an implementation of an example adjustment member in a third fabrication position.

FIG. 15H illustrates a cutaway side view of an implementation of an example sheath.

FIG. 15I illustrates a top view of an implementation of an example sheath.

FIG. 15J illustrates a posterior view of an implementation of an example sheath.

FIG. 15K illustrates a second side perspective view of an implementation of an example sheath.

FIG. 15L illustrates a second side view of an implementation of the example sheath illustrated in FIG. 15K.

Like reference symbols in the various drawings indicate like elements.

DETAILED DESCRIPTION

Figure 1:
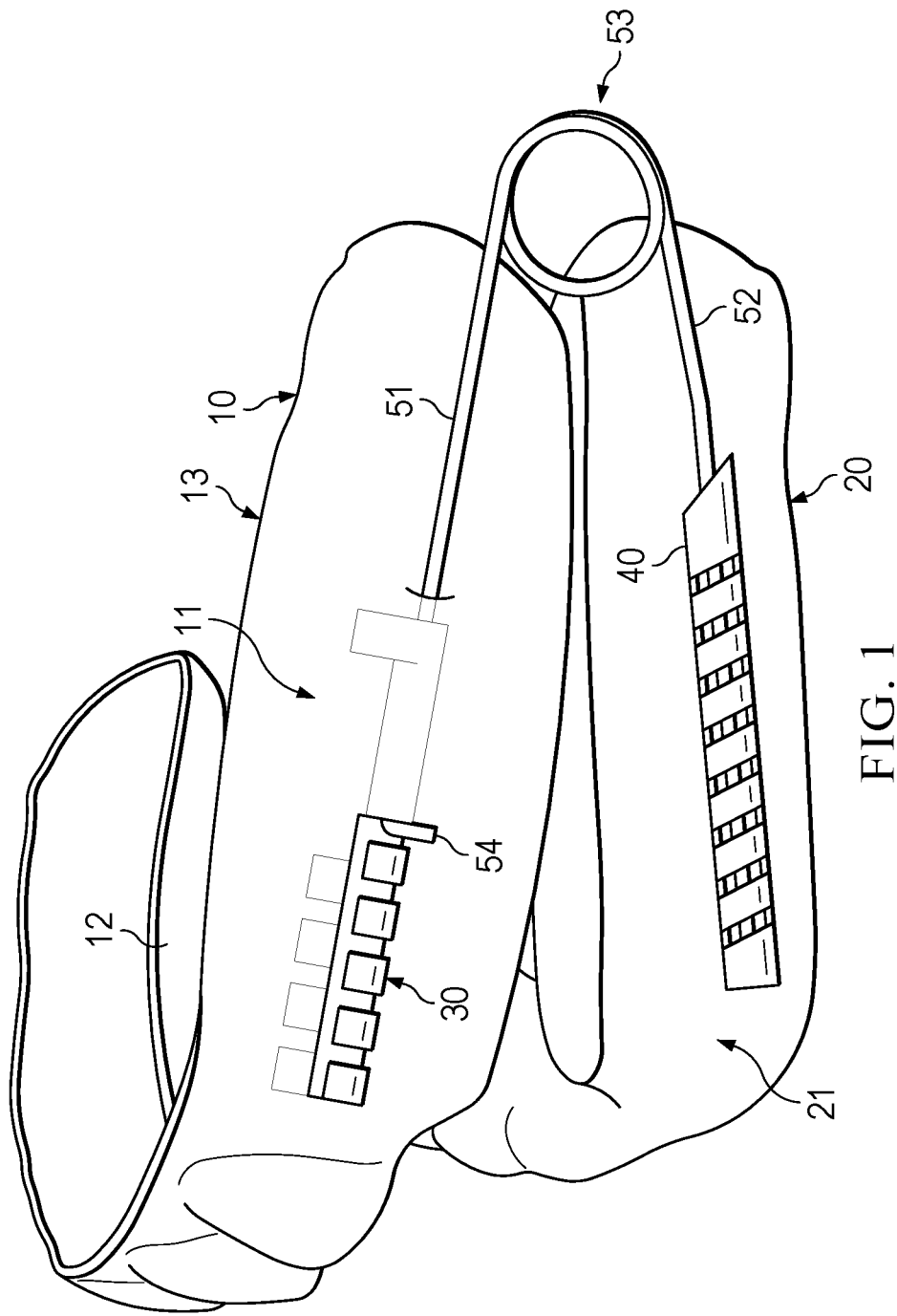
FIG. 1 illustrates first side perspective view of an implementation of an example dental appliance.

In various implementations, a dental appliance may be provided to increase the airway of a user. During use, the dental appliance may move the mandible of a user from an initial position relative to the maxilla to an adjusted position that is a more forward second position (e.g., closer to the anterior side of the user). The movement may be temporary. When the dental appliance is removed, the mandible may return to approximately the initial position. Thus, users with orthodontic adjustments (e.g., past and/or current) may utilize the dental appliance without substantially damaging the orthodontic adjustments.

By increasing the airway of a user (e.g., increasing the gap through which air can be drawn in the mouth and/or throat), snoring may be reduced and/or inhibited. Increasing the airway of a user may improve a user's health (e.g., due to greater air intake, decreased snoring, decreased drowsiness due to lack of sleep, etc.). In some implementations, symptoms of sleep apnea may be decreased when using the dental appliance since the airway may be increased.

In various implementations, the dental appliance may include an attachment member and a sheath coupled via a connector. The dental appliance may be single sided and/or double sided (e.g., may be disposed on one or two opposing sides of a user's mouth). The attachment member and/or sheath may be directly and/or indirectly coupled to the mouth of a user. For example, the attachment member and/or sheath may be coupled to one or more teeth via bite plates, orthodontic bases, and/or orthodontic brackets. The dental appliance may be removable to allow the user to position the device to reduce snoring and/or increase airways, and then remove the device as needed (e.g., upon waking).

In various implementations, a dental appliance may include bite plates. Use of bite plates may facilitate removal of the dental appliance when not in use since bite plates may removably fit over one or more teeth. A bite plate may at least partially cover facial, occlusal, and/or lingual surfaces of one or more teeth. The bite plate may or may not include a portion that contacts the palate. In some implementations, a bite plate to be disposed on lower teeth may not extend to cover the palate to increase user comfort (e.g., since a user's comfort may decrease if the bite plate interferes with tongue placement and/or protrudes into the tongue). The bite plate may materials such as acrylic (e.g., cured acrylic resin), vinyl, thermoplastics, and/or any other appropriate material.

A bite plate may include an inner surface and an outer surface. The inner surface may be designed to receive one or more teeth. For example, the inner surface may include tooth mating surfaces that follow a contour of a tooth (e.g., at least a portion of a surface of a tooth may contact the tooth mating surface). In some implementations, at least the edges of the bite plate may contact the tooth to inhibit slipping and/or release of the bite plate from the teeth. In some implementations, a dental professional may create a mold of a patient's mouth (e.g., including teeth) or portion thereof using commercially available methods. The bite plate(s) of the dental appliance may then be made from this mold such that the inner surfaces of the bite plate are configured to have approximately corresponding shapes to the tooth over which the bite plate is positioned (e.g., the bite plate may have a generally concave surface to at least approximately match at least a portion of the generally convex surface of a tooth). In some implementations, the bite plate may or may not be custom made for a users mouth. For example, the bite plate may be designed to fit a range of users (e.g., users with a set of predetermined mouth sizes). A dental professional may obtain a kit that includes a plurality of bite plates and select bite plate(s) from the kit for use with an individual user.

The bite plate may include a lingual side and a facial side. The lingual side and the facial side may extend from the occlusal side of the bite plate. In some implementations, the bite plate may include a palate portion (e.g., extending from the lingual surface and proximate an opposing side to the occlusal side of the bite plate) that connects portions of the opposing lingual sides of the bite plate. For example, the palate portion may contact at least a portion of a palate of the user when the bite plate is disposed in a user. The portion may have a curvature similar to at least a portion of the palate (e.g., the curvature may be approximately the same as the curvature of a portion of a user's palate). The palate portion may be flexible and/or deformable to increase comfort and/or fit, while the remainder of the bite plate may be rigid to allow teeth disposed in the bite plate to be moved as a set, in some implementations.

The facial side of the bite plate may extend from the occlusal side and terminate at an end. In some implementations, the lingual side or portions thereof may extend from the occlusal side and terminate in an end.

The bite plate may cover a tooth or a portion thereof, several teeth or portions thereof, and/or the bite plate may fit over the entire set of teeth (e.g., an upper set and/or lower set). For example, the bite plate may fit over at least portion of each tooth in a set of teeth (e.g., upper set of teeth or lower set of teeth).

The bite plate may be at least partially rigid. In some implementations, the bite plate may have a rigidity to allow teeth to be moved as a set. For example, if a commercially available flexible mouth guard was utilized rather than the bite plate as described, the forces exerted on the bite plate would not be transmitted to the teeth but rather cause strain on the bite plate (e.g., and may damage the bite plate). The bite plate may have a rigidity that allows the bite plate to frictionally fit onto teeth to inhibit the bite plate from inadvertently slipping (e.g., during sleep, drinking, talking, etc.). For example, the bite plate may retain the bite plate on teeth with a greater force than the force required to overcome the spring portion of the connector (e.g., thus, when a user moves the mandible laterally and/or longitudinally, the mandible moves rather than the bite plate slipping off the teeth).

The bite plate may be at least partially deflectable, in some implementations, to facilitate placement in the mouth. For example, facial and/or lingual surfaces of a bite plate may deflect when the bite plate is positioned in a user's mouth. The deflectability may increase stability of the bite plate in the mouth since gaps between a tooth and the bite plate and/or a portion of the bite plate may be decreased by allowing at least partially deflectable portions on the lingual and/or facial surfaces on the bite plate. For example, an end of the lingual and/or facial sides of bite plate may contact a surface of one or more teeth to frictionally retain the bite place in a predetermined position. In some implementations, by allowing end(s) of the bite plate to deflect, the bite plate may more comfortably be positioned in a user and/or more of the end of the bite plate may contact tooth/teeth to create a more secure placement. In some implementations, at least a portion of the lingual and facial surface of the bite plate may be thinner than other portions of the bite plate, to allow flexibility.

Figure 2:
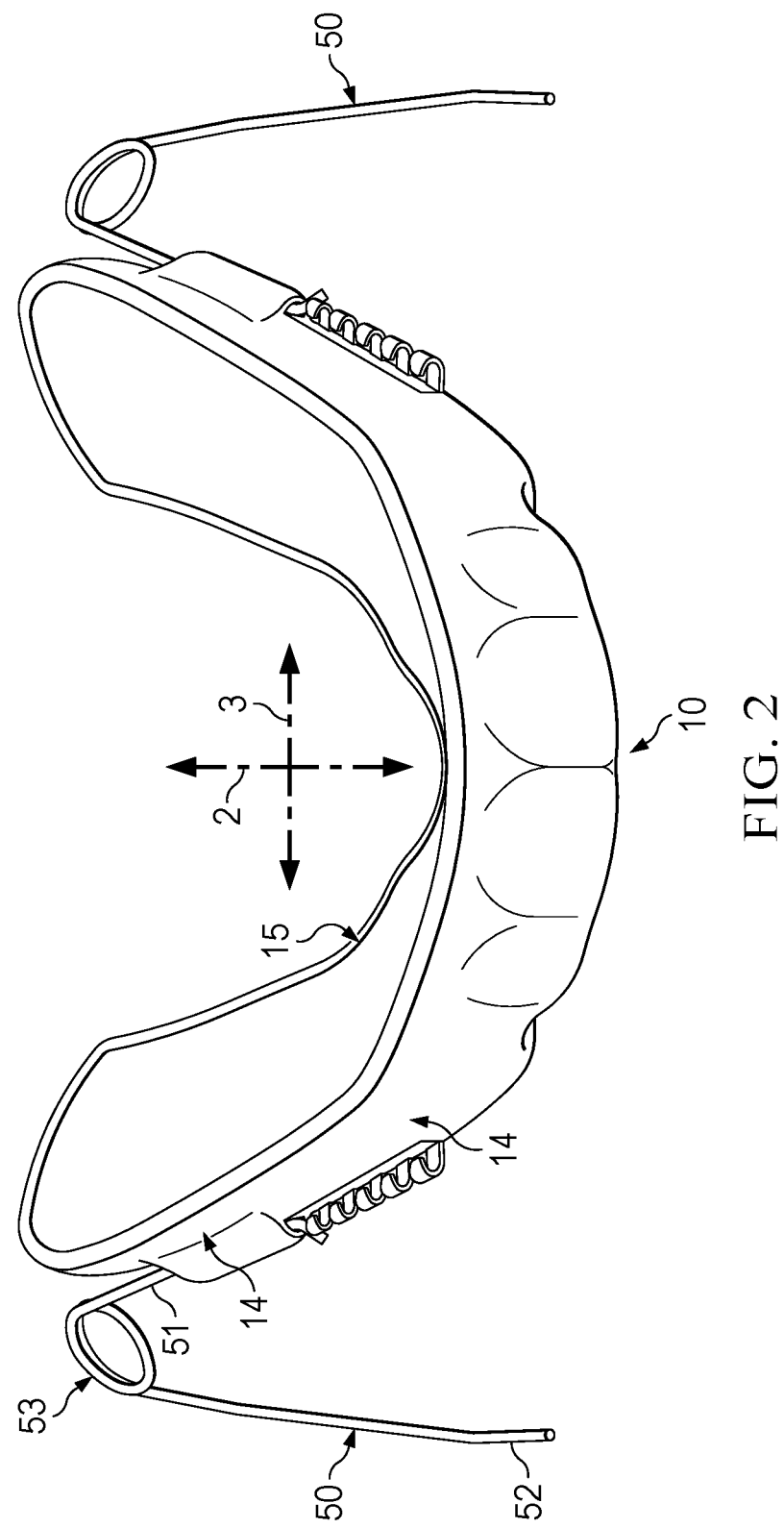
FIG. 2 illustrates top view of an implementation of an upper portion of an example dental appliance.
Figure 3:
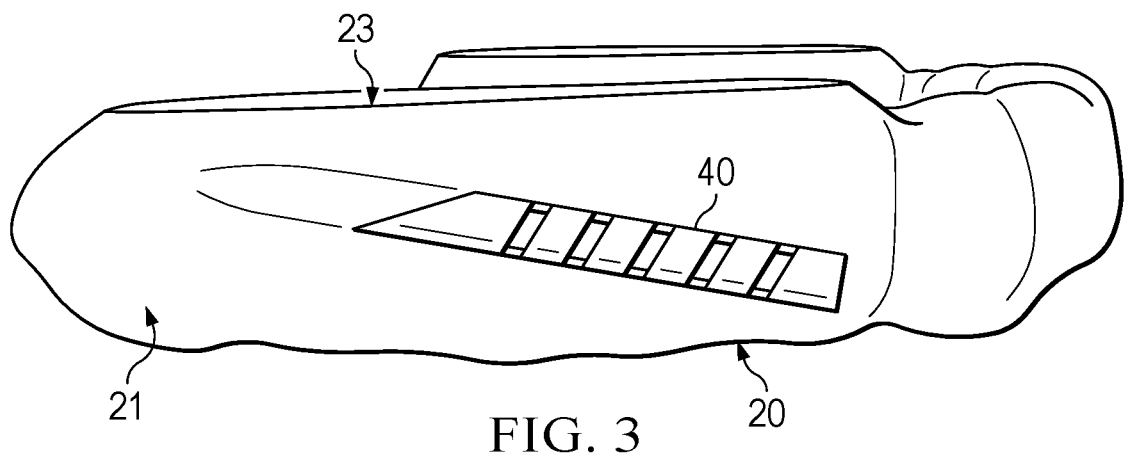
FIG. 3 illustrates a second side view of an implementation of a lower portion of an example dental appliance.
Figure 4:
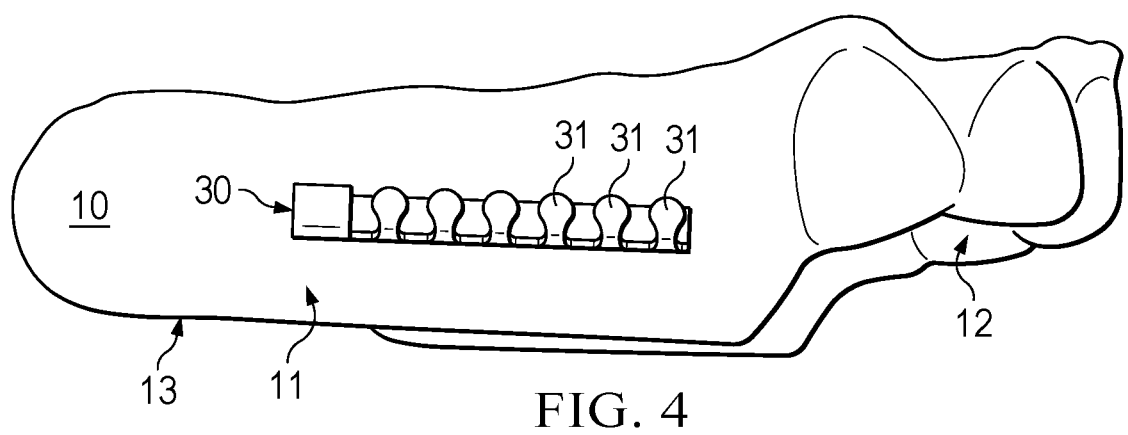
FIG. 4 illustrates a second side view of an implementation of an upper portion of an example dental appliance.
Figure 5:
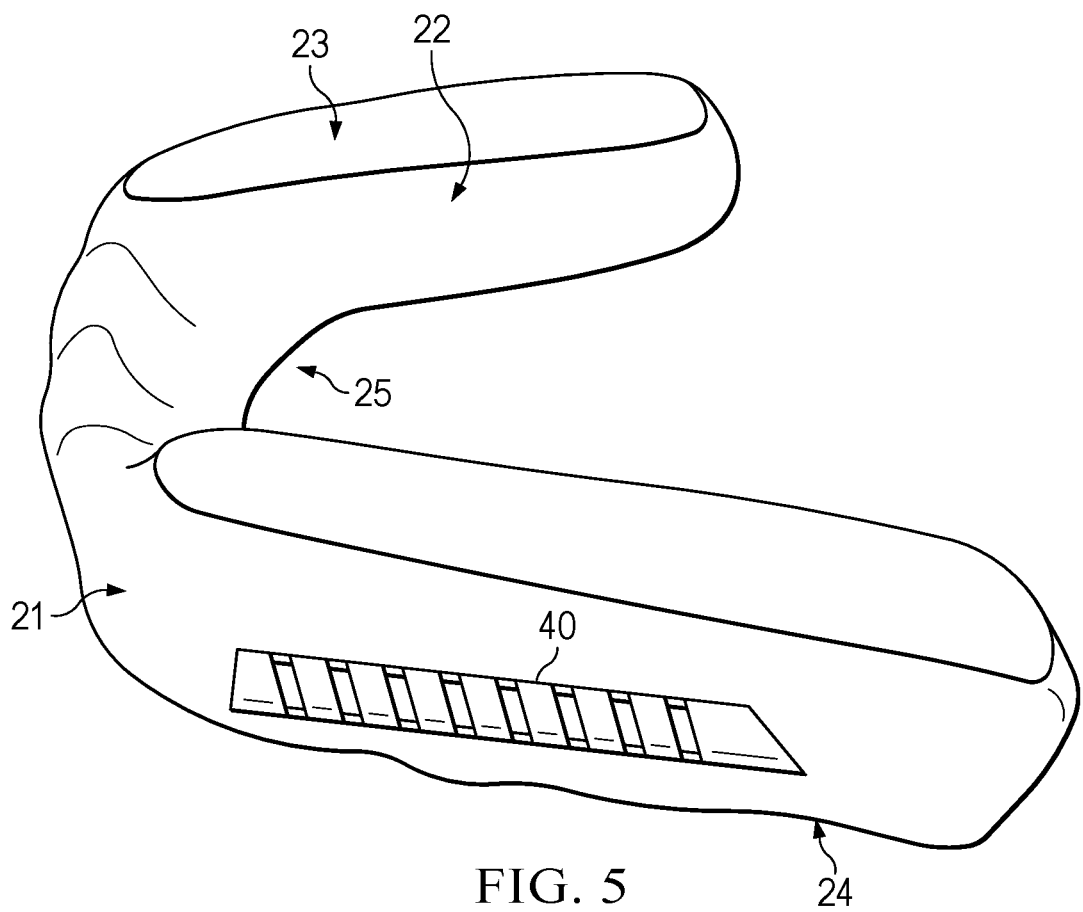
FIG. 5 illustrates a first side perspective view of a lower portion of an implementation of an example dental appliance.
Figure 6:
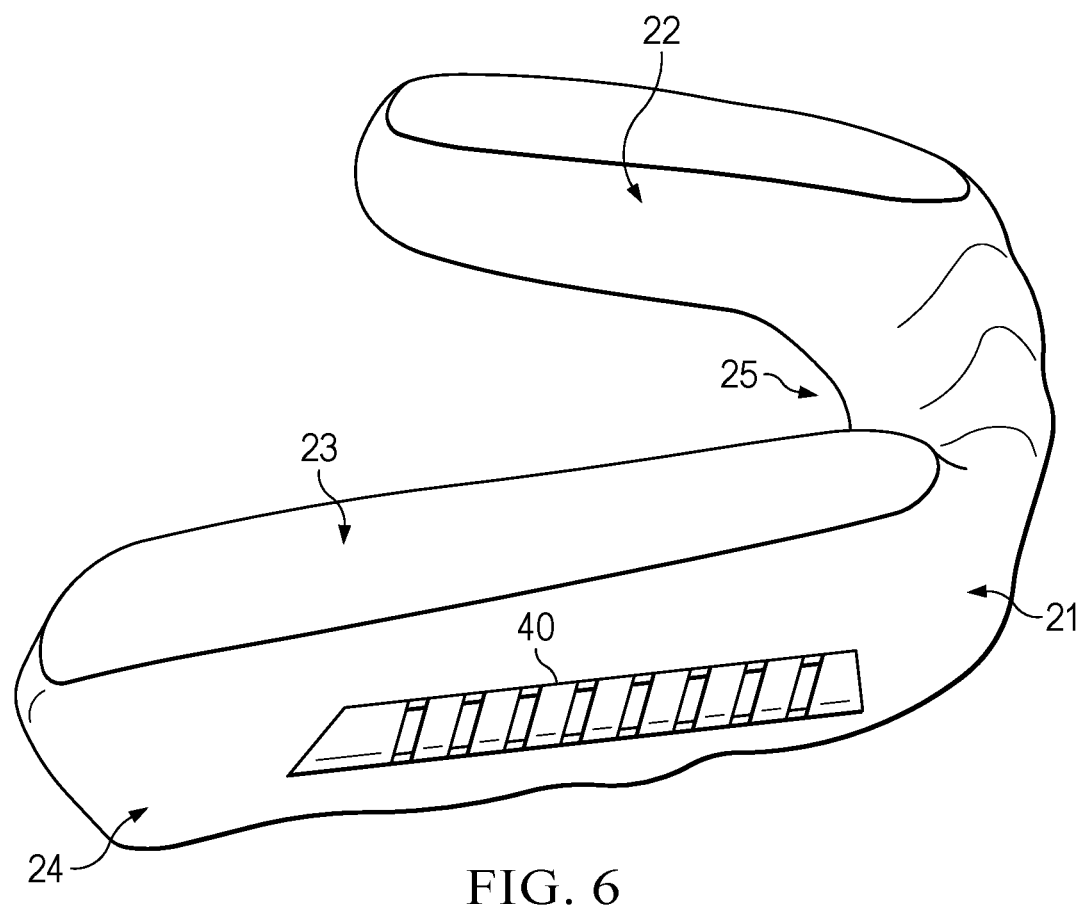
FIG. 6 illustrates a second side perspective view of an implementation of a lower portion of an example dental appliance.
Figure 7:
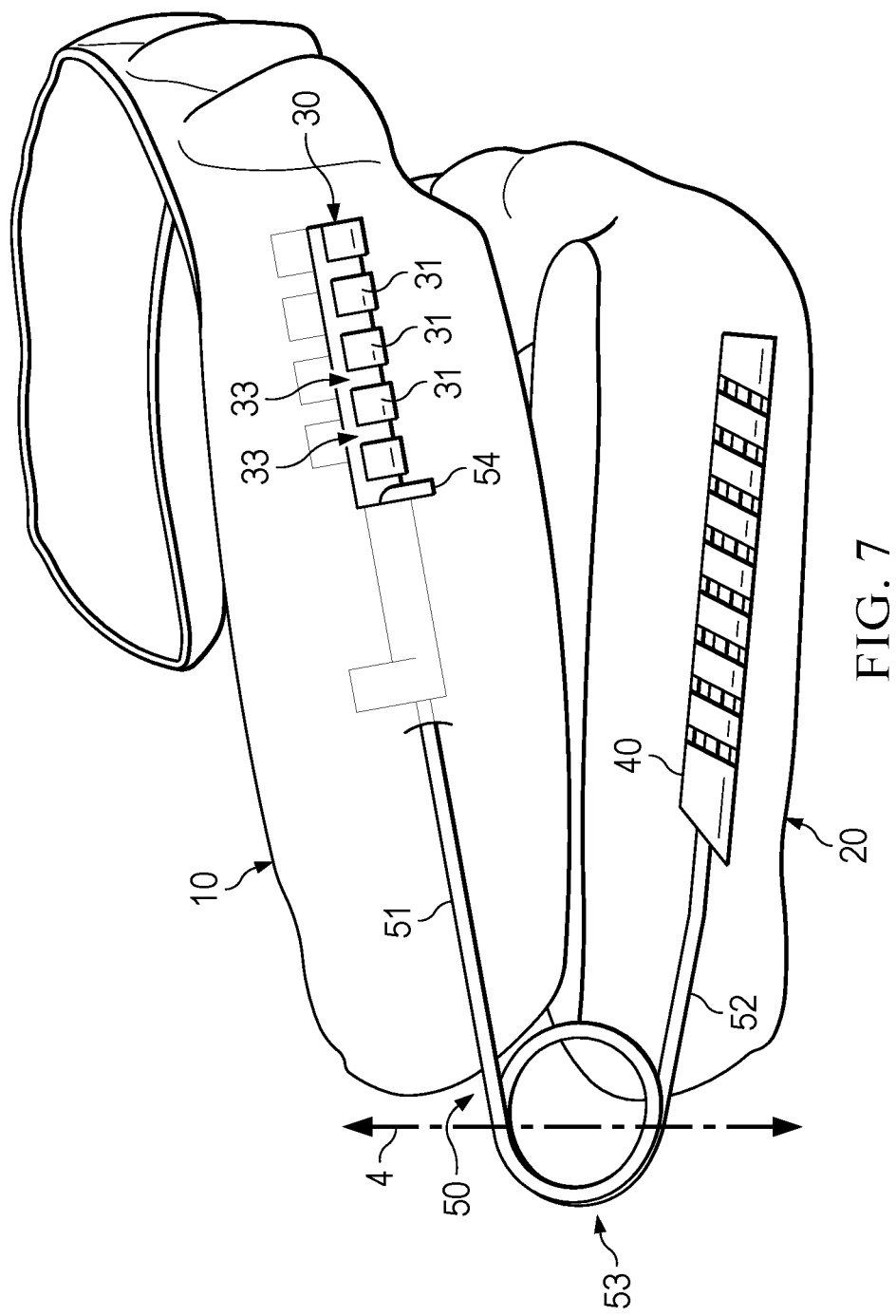
FIG. 7 illustrates a second side perspective view of an implementation of an example dental appliance.
Figure 8:
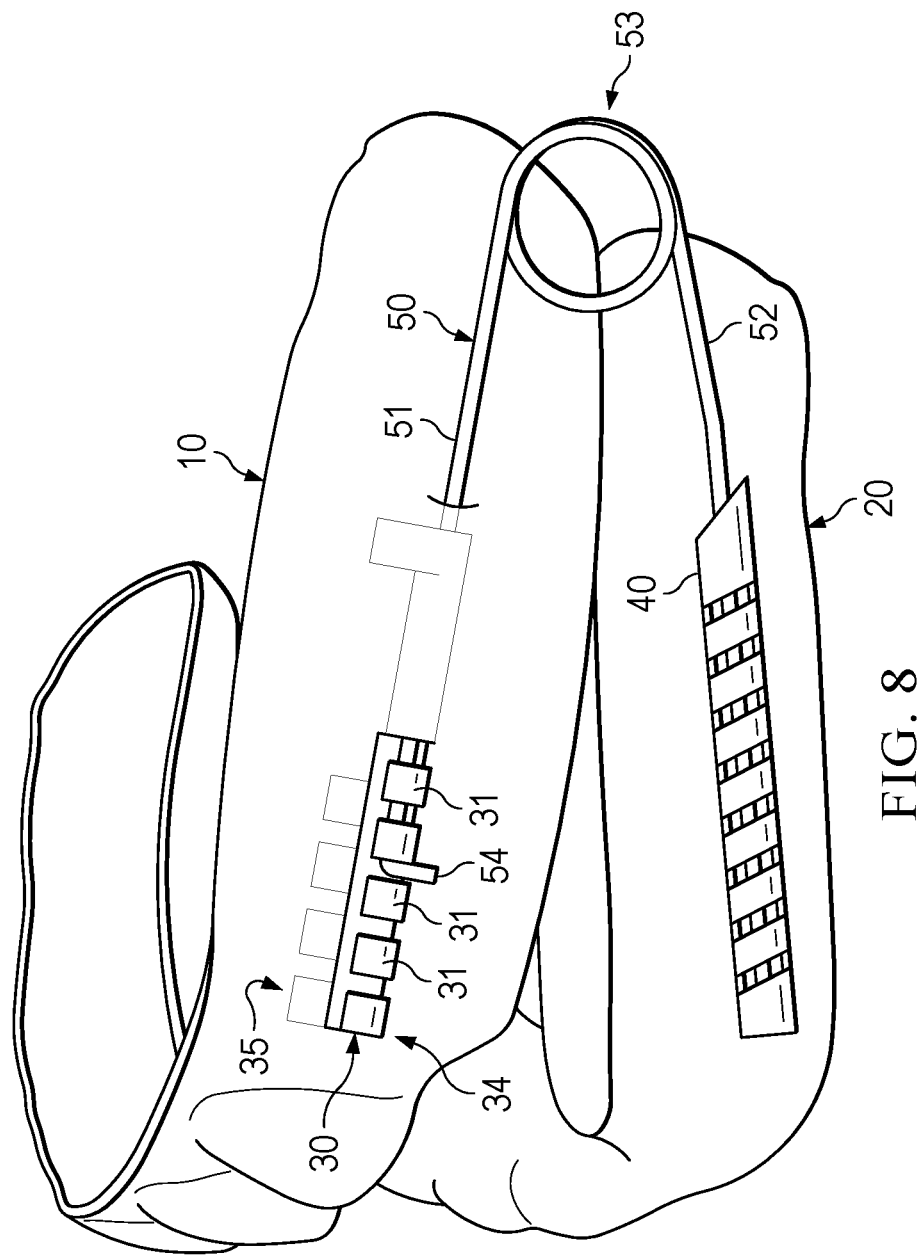
FIG. 8 illustrates a first side perspective view of an implementation of an example dental appliance in a first position.
Figure 9:
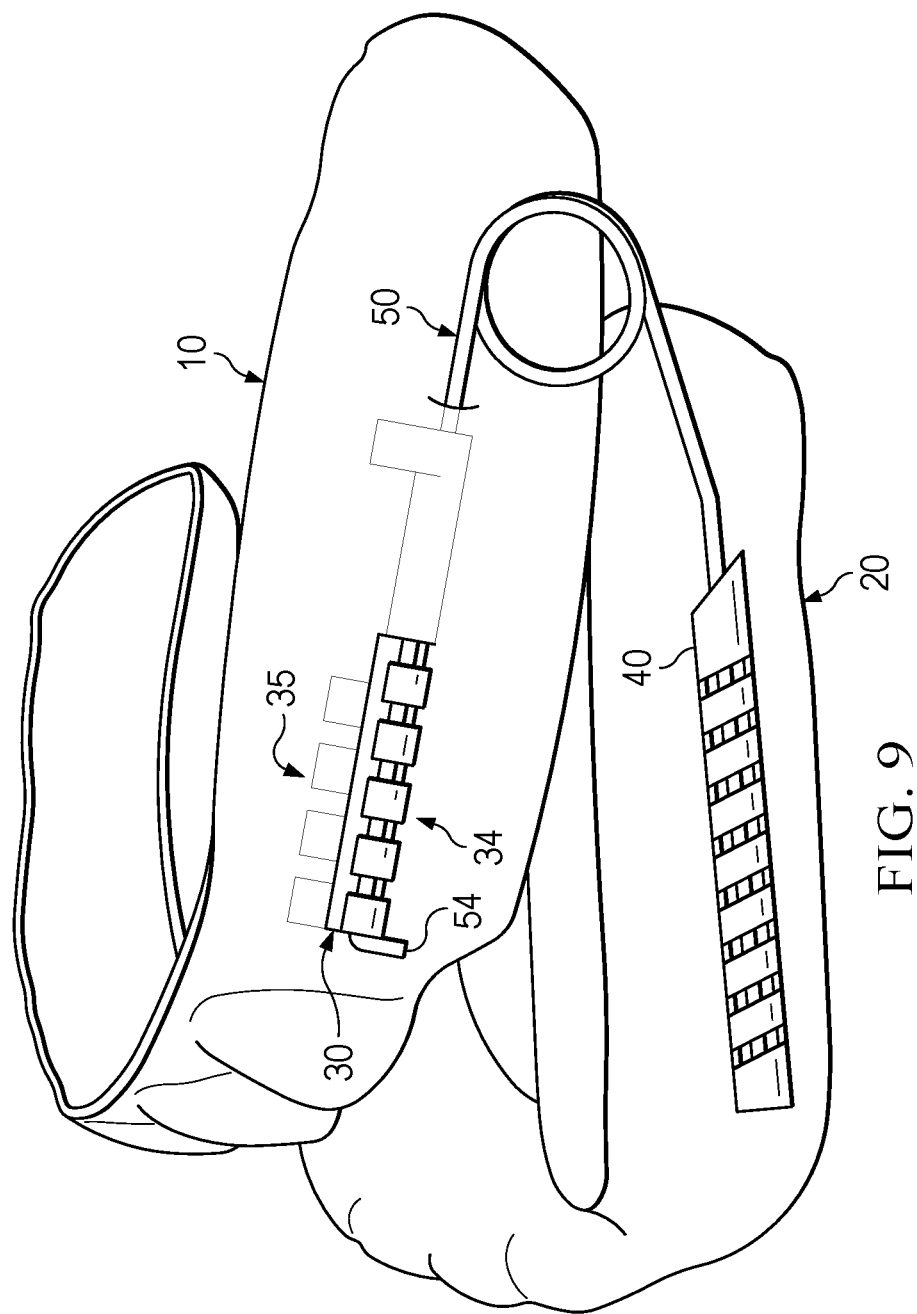
FIG. 9 illustrates a first side perspective view of an implementation of the example dental appliance, illustrated in FIG. 8, in a second position.
Figure 10:
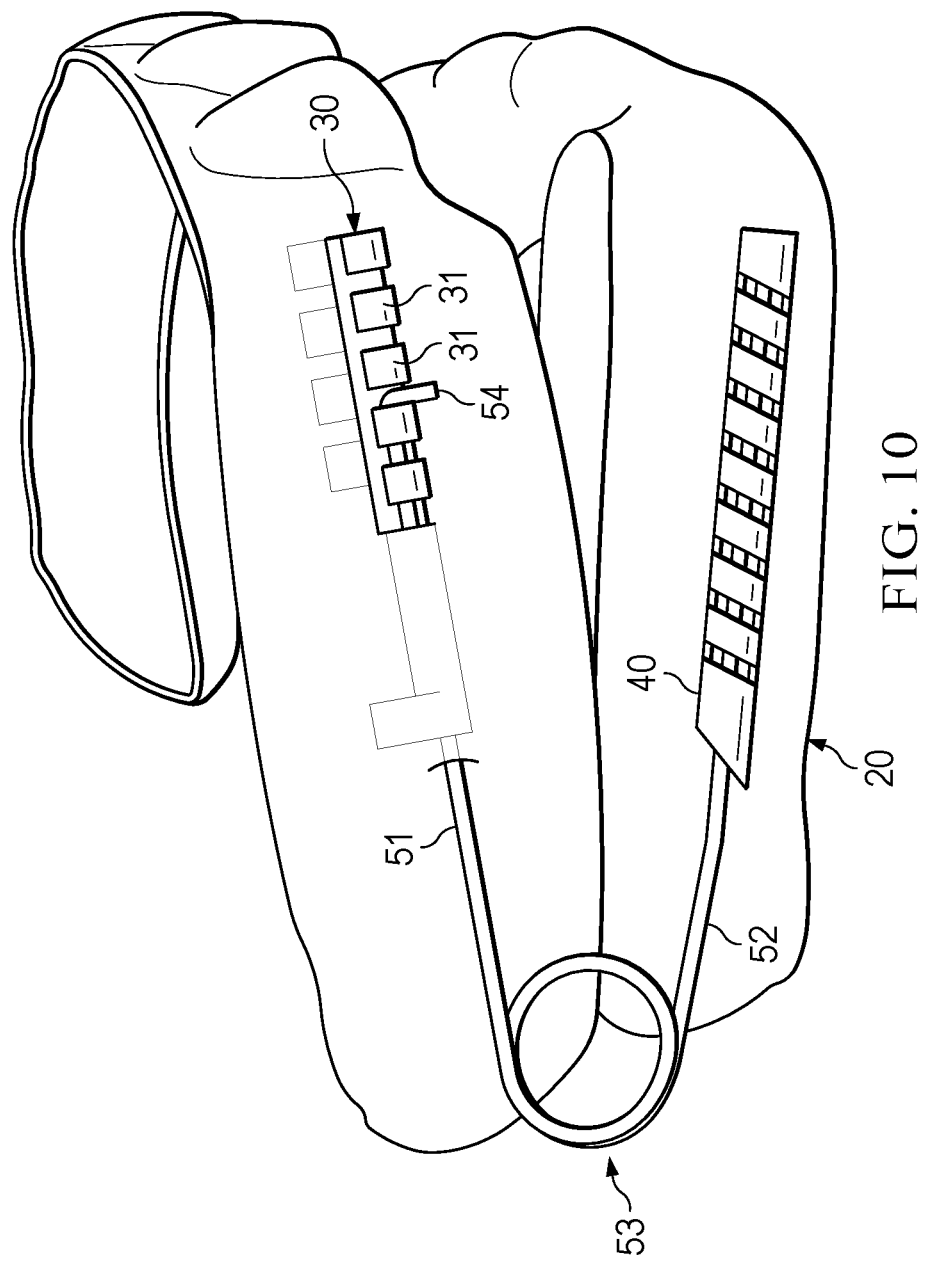
FIG. 10 illustrates a second side perspective view of an implementation of an example dental appliance in a first position.
Figure 11:
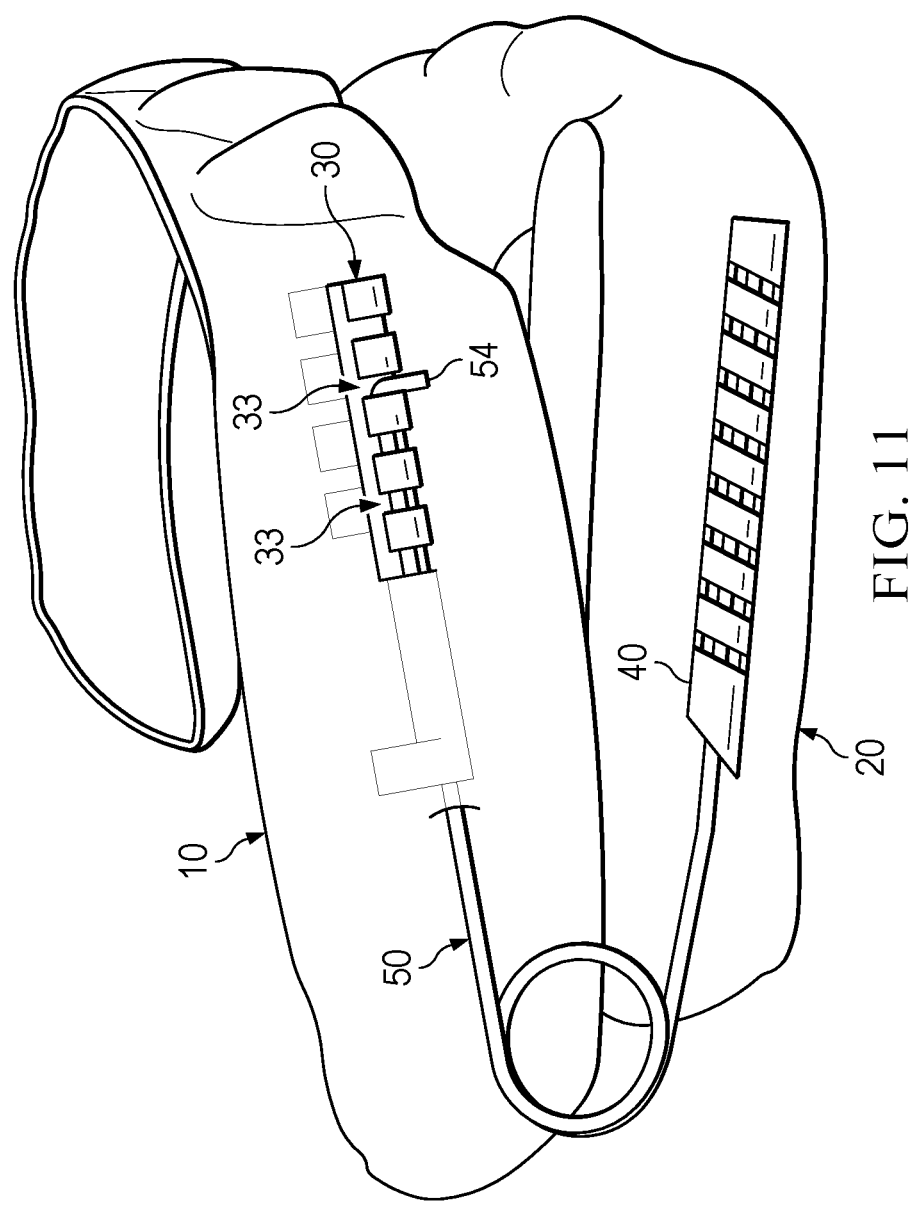
FIG. 11 illustrates a second side perspective view of an implementation of the example dental appliance, illustrated in FIG. 10, in a third position.
Figure 12:
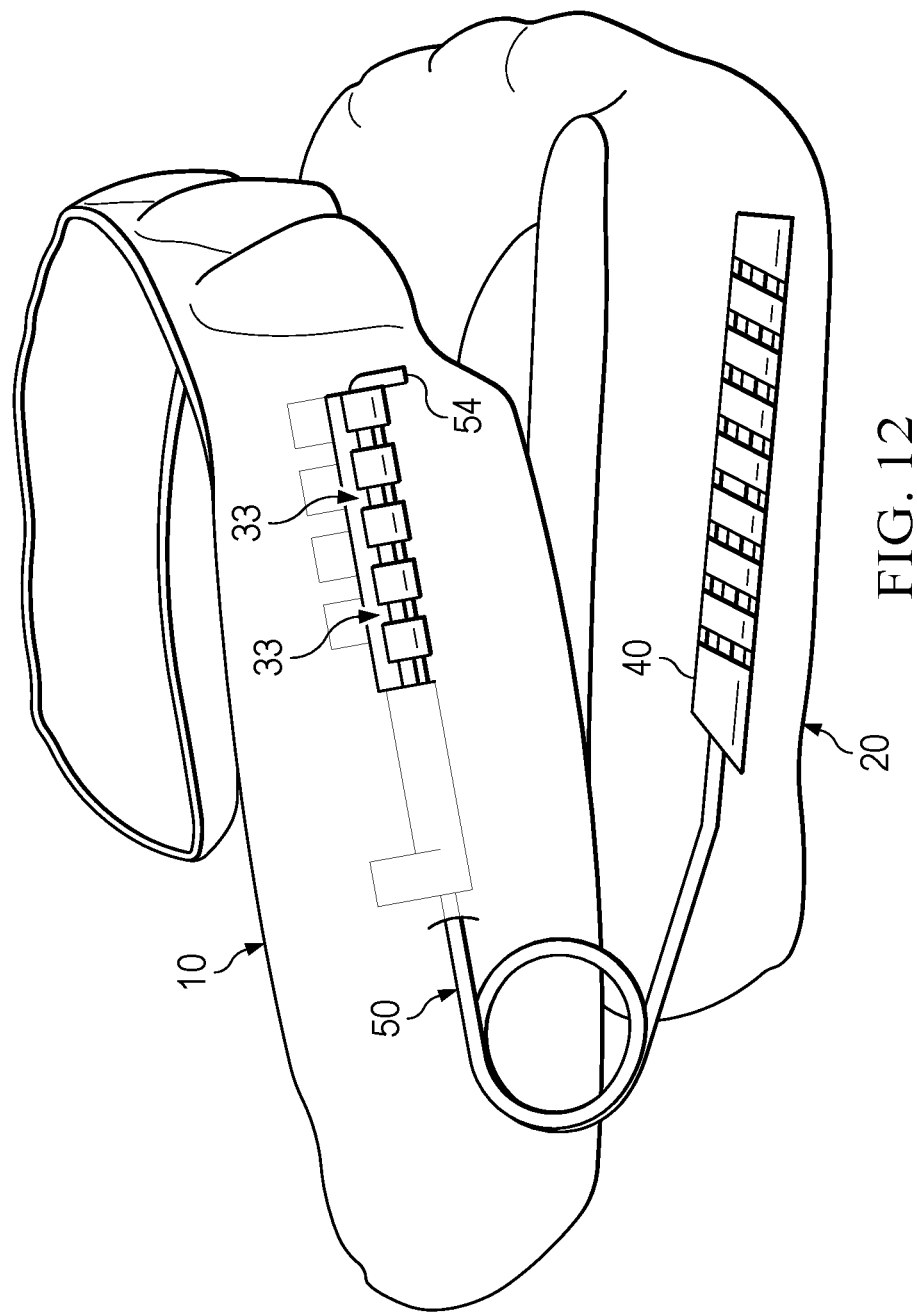
FIG. 12 illustrates a second side perspective view of an implementation of the example dental appliance, illustrated in FIG. 10, in a second position.

FIGS. 1-10 illustrate a variety of views of implementations of example dental appliances or portions thereof. FIG. 1 illustrates a side perspective view of an implementation of a dental appliance, and FIG. 2 illustrates top view of an implementation of an example dental appliance. FIG. 3 illustrates a second side view of an implementation of a lower portion of a dental appliance, and FIG. 4 illustrates a second side view of an implementation of an upper portion of a dental appliance. FIG. 5 illustrates a first side perspective view and FIG. 6 illustrates a second side perspective view of a lower portion of an implementation of a dental appliance. FIG. 7 illustrates a second side perspective view of an implementation of an example dental appliance. FIG. 8 illustrates a first side perspective view of an implementation of an example dental appliance in a first position and FIG. 9 illustrates the example dental appliance in a second position. FIG. 10 illustrates a second side perspective view of an implementation of a dental appliance in a first position, FIG. 11 illustrates the dental appliance in a third position, and FIG. 12 illustrates the dental appliance in a second position.

As illustrated, the dental appliance 1 includes a first bite plate 10 and a second bite plate 20. The first bite plate may be disposed on upper teeth (e.g., teeth disposed in the maxilla), during use. The first bite plate 10 may include a facial side 11, a lingual side 12, and an occlusal side 13. The inner surface(s) of the facial side and/or the lingual side may have tooth mating surfaces to receive at least a portion of the teeth to which the bite plate will be coupled. The occlusal side may or may not have a shape to receive occlusal side(s) of teeth to which the bite plate will be coupled. The facial side 11 may extend from the occlusal side 13 of the bite plate and may terminate at a facial end 14. As illustrated, the lingual side of the bite plate may extend from the occlusal side 13 and terminate at a lingual end 15. A palate portion may or may not extend between lingual portions on opposing sides (e.g., corresponding to opposing sides of a user's mouth) of the bite plate.

The second bite plate 20 may be disposed on lower teeth (e.g., teeth disposed in the mandible), during use. The second bite plate 20 may include a facial side 21, a lingual side 22, and an occlusal side 23. The inner surface(s) of the facial side and/or the lingual side may have tooth mating surfaces to receive at least a portion of the teeth to which the bite plate will be coupled. The occlusal side may or may not have a shape to receive occlusal side(s) of teeth to which the bite plate will be coupled. The facial side 21 may extend from the occlusal side 13 of the bite plate and may terminate at a facial end 24. As illustrated, the lingual side of the bite plate may extend from the occlusal side 23 and terminate at a lingual end 25.

The dental appliance may include an adjustment member 30. The adjustment member may be coupled to the first bite plate, in some implementations. The adjustment member may be coupled to a surface of the first bite plate and/or at least partially disposed in the first bite plate. For example, at least a portion of the adjustment member may be disposed in the first bite plate to reduce the portion of the adjustment member that extends above a surface of the facial side of the first bite member. This may increase user comfort, in some implementations.

As illustrated, the adjustment member 30 may be coupled to the facial side 11 of the first bite plate 10. Coupling the adjustment member to the facial side of the first bite plate may increase comfort for a user wearing the dental appliance since the adjustment member may not contact the tongue (e.g., which may cause discomfort and/or damage) and/or interfere with the natural position of the tongue in the mouth. In some implementations, the adjustment member may be coupled to the lingual side of the first bite plate. For example, the user may prefer that the adjustment member may not contact the lip and/or checks (e.g., sensitive skin prone to damage, appearance, etc.). In some implementations, the user may prefer that the adjustment member be coupled on the lingual side for aesthetic reasons.

Figure 13:
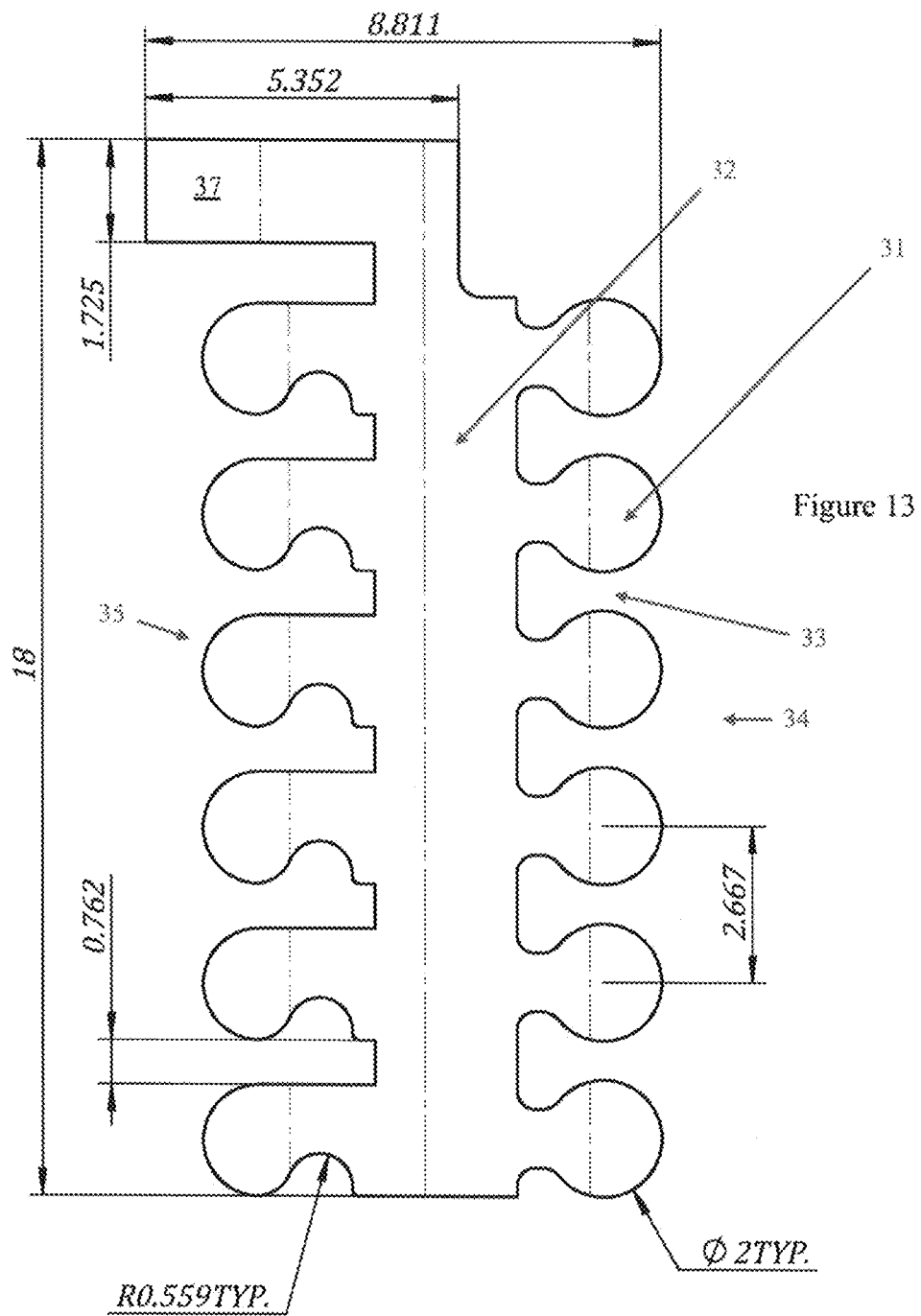
FIG. 13 illustrates an implementation of an example adjustment member.

The adjustment member 30 may include one or more protrusions 31. As illustrated in FIGS. 13-14G, the adjustment member may include a spine 32 and a plurality of protrusions 31 extending from the spine. As illustrated in FIG. 13, the adjustment member may, in some implementations, be manufactured and/or provided to the dental professional as a planar member. The manufacturer and/or dental professional may adjust (e.g., bend) the adjustment member to a predetermined shape. For example, the adjustment member may include a material that is flexible (e.g., capable of being bent for example by hand or with tool). The adjustment member may be flexible but rigid enough to resist deformation under the force to move the mandible forward. In some implementations, the adjustment member may be adjusted (e.g., curvature, size, etc.) by the dental professional based on user information (e.g., mouth size, shape, contour, age, etc.). In some implementations, the adjustment member may be provided to the dental professional in a predetermined shape and the dental professional may utilize the adjustment member in the predetermined shape and/or adjust the size and/or shape of the adjustment member. In some implementations, one or more ends or portions thereof of the adjustment member proximate the lingual surfaces may be slanted (e.g., spine guide member and/or protrusion). In some implementations, angled ends may increase user comfort.

Figure 14D:
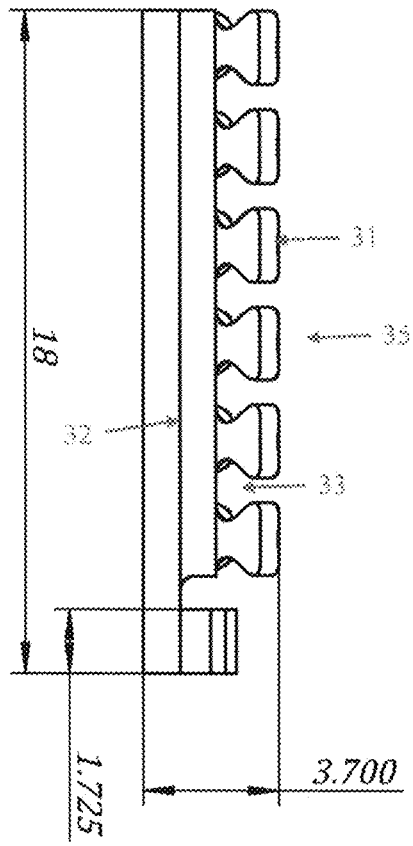
FIG. 14D illustrates a posterior view of an implementation of an example adjustment member.
Figure 14E:
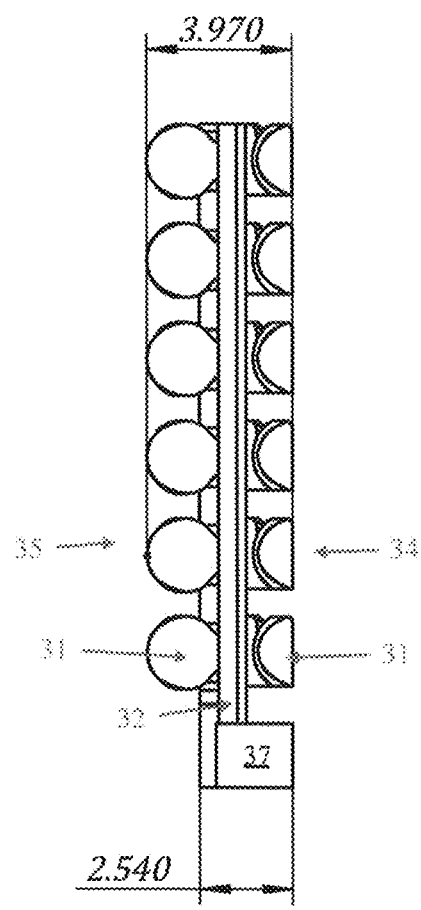
FIG. 14E illustrates an anterior view of an implementation of an example adjustment member.
Figure 14F:
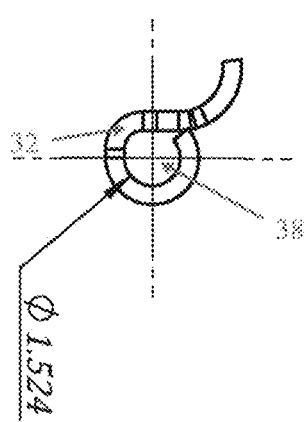
FIG. 14F illustrates a side view of an implementation of an example adjustment member.
Figure 14G:
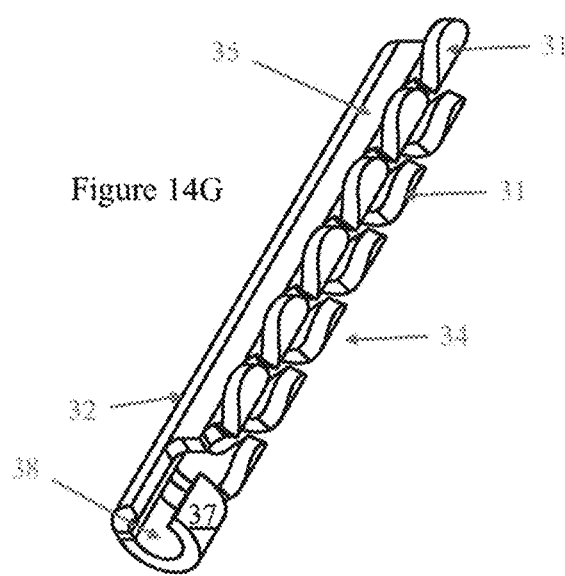
FIG. 14G illustrates a top view of an implementation of an example adjustment member.

As illustrated in FIGS. 13 and 14A, the adjustment member 30 may be adjusted from a planar member to create an adjustment member with a predetermined shape. The adjustment member may have any appropriate size and/or shape. The adjustment member may include a facial side 34 and an opposing coupling side 35 (e.g., more proximate the lingual side of the teeth than the facial side of the adjustment member). The facial side of the adjustment member and/or the spine guide member 37 may be bent to a predetermined shape. For example, the protrusions on the facial side, spine, and/or spine guide member may be bent inwards into an approximately curved shape, as illustrated in FIG. 14B. The protrusions, spine and/or spine guide member may be bent into similar curved shapes, in some implementations. The facial side or portions thereof may be bent such that the facial side or portions thereof are capable of receiving a portion of the connector. For example, a portion first arm of the connector may be disposed proximate the curved protrusions of the facial side of the attachment member. The coupling side of the adjustment member and/or spine guide may be bent into a predetermined shape. For example, the protrusions on the coupling side, spine, and/or spine guide member may be bent in a direction away from the protrusions on the facial side of the adjustment member, as illustrated in FIG. 14C. As illustrated in FIGS. 14C-14G, in some implementations, the protrusions on the facial side and the coupling side may be bent (e.g., curved, slanted, etc.) in the same direction. The curvature of the protrusions may be similar and/or different from each other.

As illustrated, protrusions may be disposed along a length of a spine. The protrusions may be disposed on a first side and/or on an opposing second side of the spine. The protrusions on the same side may be similarly bent, as illustrated. Some protrusion(s) on a side of the spine may be bent while other protrusion(s) may not be bent, in some implementations. The bent protrusions may have or may not have similar curvatures to each other on a single side of the spine.

In various implementations, the protrusion(s) on the facial side of the adjustment member may have a curved portion. The curved portion may curve towards the coupling side of the adjustment member, in some implementations. A gap 33 may be disposed between two adjacent protrusions. An opening 38 may be disposed through the curved spine guide member (e.g., to allow a portion of the connector to be disposed through the spine guide member). The size opening may be determined by the curvature of the protrusions.

The protrusions 31 on the coupling side of the adjustment member 30 may be coupled to the first bite plate 10. For example, the protrusions on the coupling side of the adjustment member 30 may be at least partially imbedded in the bite plate. In some implementations, prior to curing the bite plate, a portion of the adjustment member (e.g., at least a portion of the protrusions on the coupling side) and/or at least a portion of the spine guide member 37 may be at least partially embedded in the bite plate. For example, the bite plate may extend to cover at least a portion of the protrusions on the coupling side and/or the spine guide member (e.g., such that the opening disposed in the spine guide member is accessible) The bite plate may then be cured (e.g., heat and/or light) and the adjustment member may be coupled to bite plate (e.g., since the cured material may be disposed in the gaps between the protrusions on the coupling side, the cured material may secure the adjustment member to the bite plate). In some implementations, the adjustment member may be otherwise coupled (e.g., glued, bonded, etc.) to the first bite plate 10.

The dental appliance may include a sheath 40. The sheath may be coupled to the second bite plate. The sheath may be coupled to a surface of the second bite plate and/or at least partially disposed in the second bite plate. The sheath may be disposed on the same side or on a different side of the teeth as the attachment member. For example, a sheath and an attachment member may be disposed on the facial surface of a first side of the dental appliance. A sheath and an attachment member may be disposed on the lingual surface of a first side of the dental appliance. In some implementations, a sheath may be disposed proximate a facial side of the lower teeth and an attachment member may be disposed proximate the lingual side of the upper teeth.

Figure 15A:
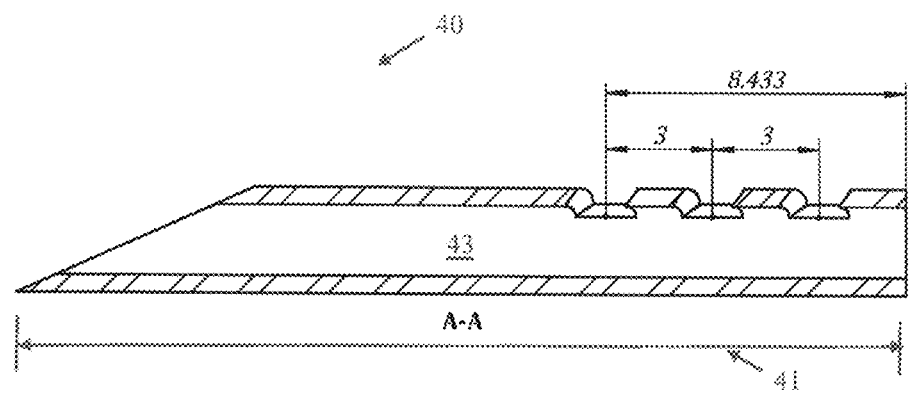
FIG. 15A illustrates a cutaway view of an implementation of an example sheath.
Figure 15B:
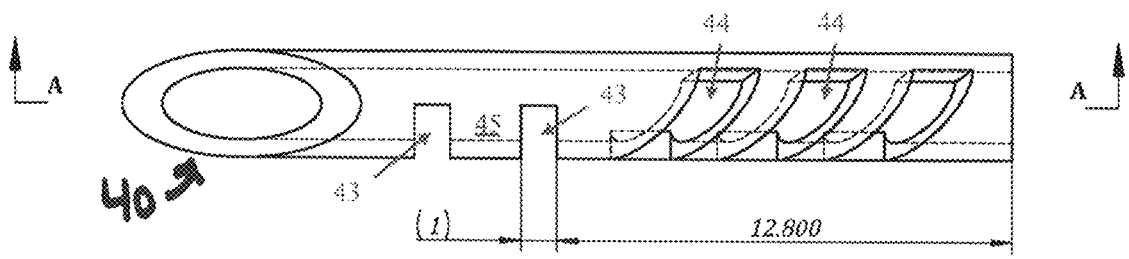
FIG. 15B illustrates an top view of an implementation of an example sheath.
Figure 15C:
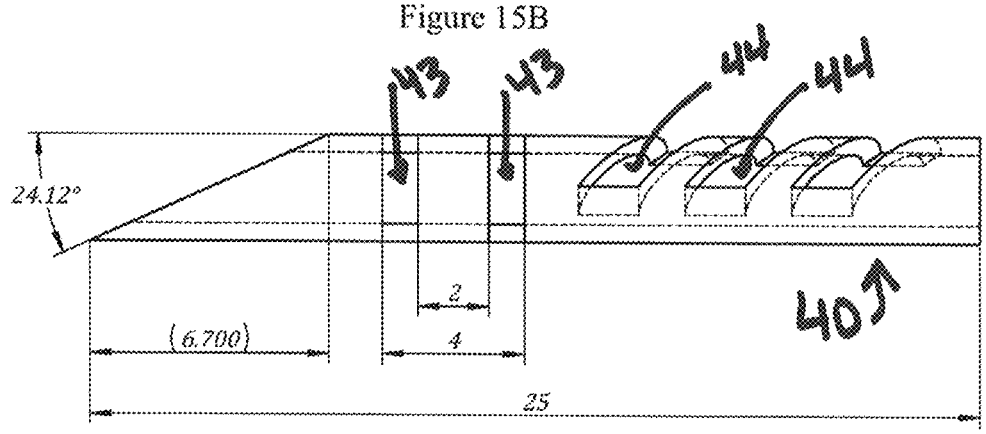
FIG. 15C illustrates an posterior view of an implementation of an example sheath.
Figure 15D:
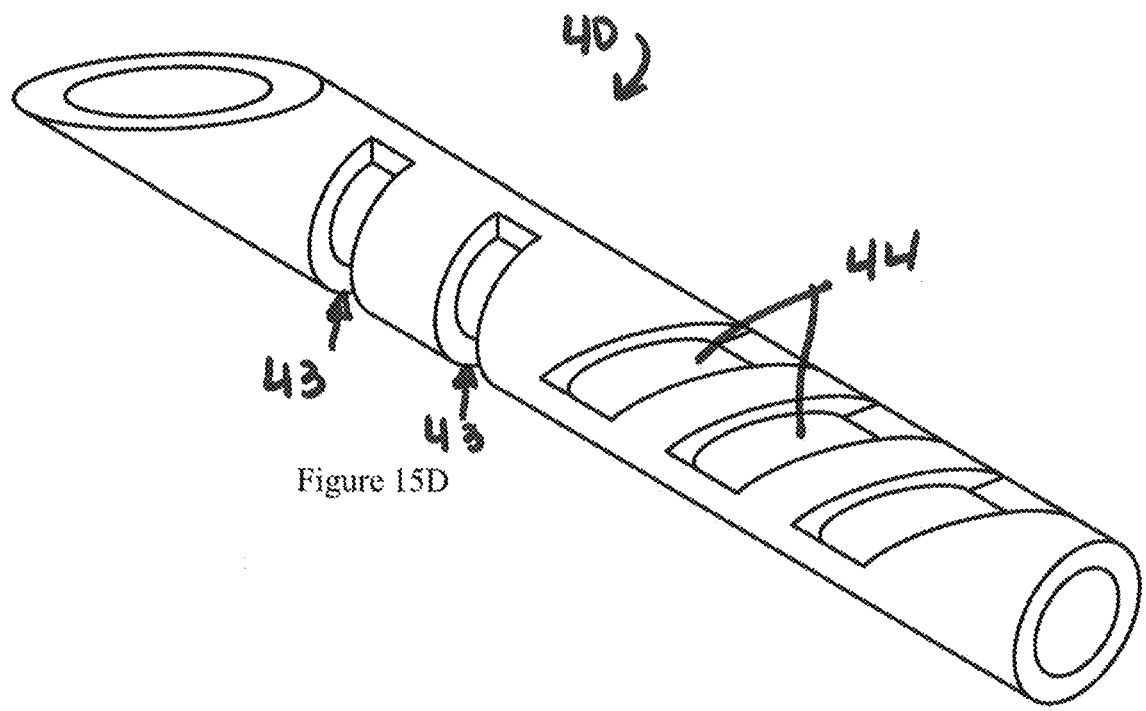
FIG. 15D illustrates a side perspective view of an implementation of an example sheath.
Figure 15E:
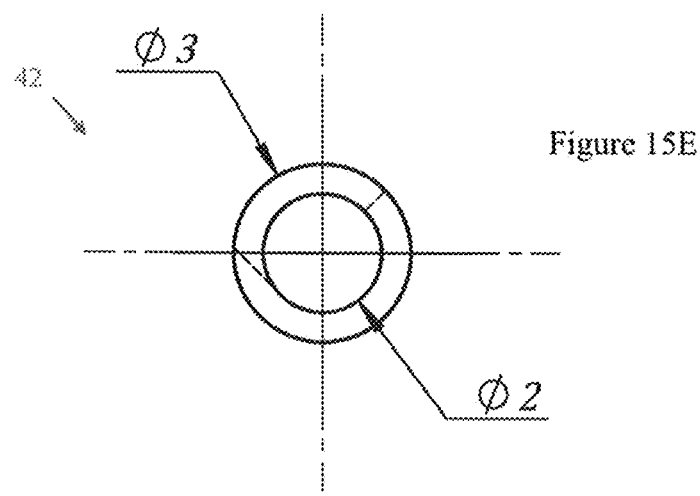
FIG. 15E illustrates a side view of an implementation of the example sheath illustrated in FIG. 15D.
Figure 15G:
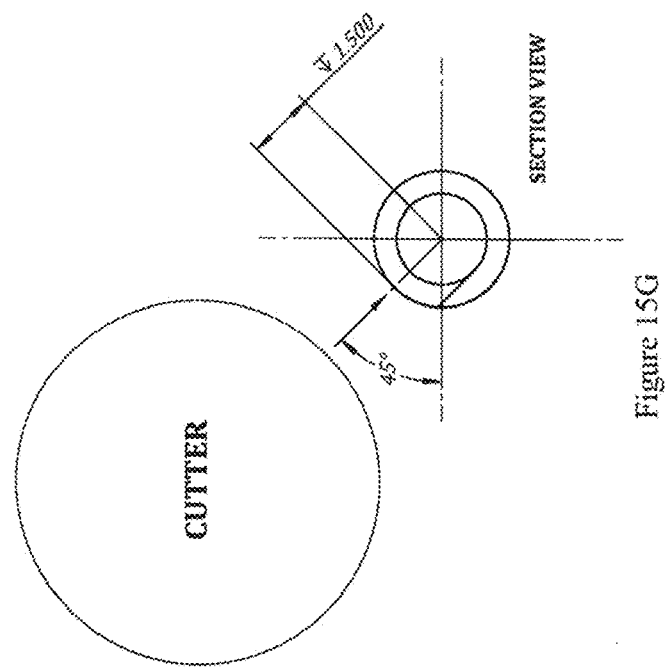
FIG. 15G illustrates a side view of an implementation of the example sheath illustrated in FIG. 15F.
Figure 15F:
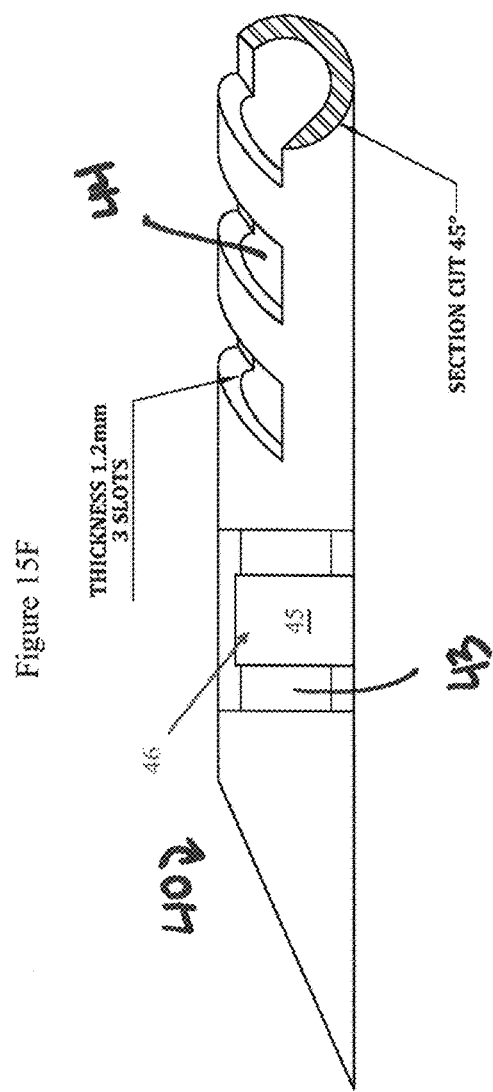
FIG. 15F illustrates a cutaway view of an implementation of a portion of an example sheath.
Figure 15M:
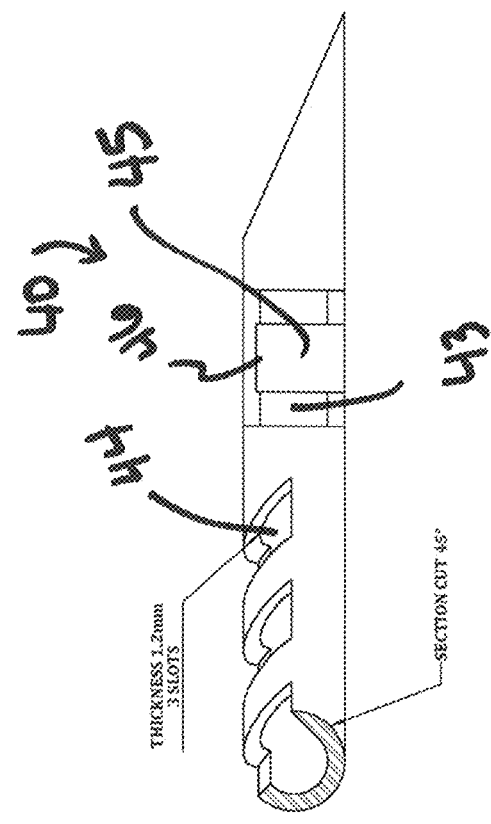
FIG. 15M illustrates a anterior view of an implementation of a portion of an example sheath.
Figure 15N:
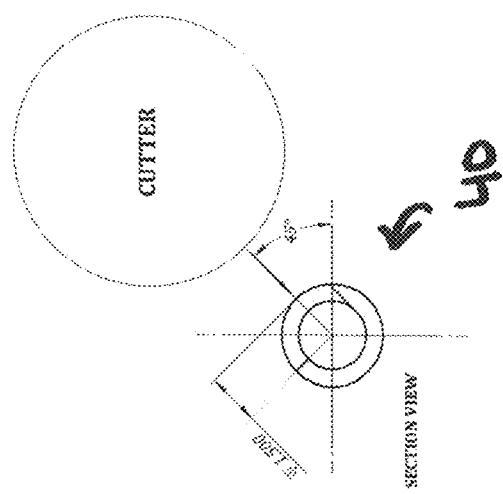
FIG. 15N illustrates a side view of an implementation of the portion of the example sheath illustrated in FIG. 15M.

The sheath may be any appropriate size and/or shaped conduit. In some implementations, a dental professional may have a kit of different sizes and/or shapes of sheaths and may select a sheath from the kit based on user information (e.g., size of mouth, amount of customization selected, age, etc.). In some implementations, the sheath may be provided to the dental professional in a predetermined size and/or shape and the dental professional may or may not customize the sheath (e.g., cut to a specified length). FIGS. 15A-15N illustrate various views of an implementation of a sheath. The sheath 40 may have a length 41 and a cross-section 42. The sheath may include a cavity 41 disposed at least partially through a length 41 of the sheath. The sheath 40 may include one or more apertures. The apertures may facilitate cleaning of the sheath. For example, since portions (e.g., inner surfaces) of the sheath (e.g., cavity 41) may be exposed to food and/or drinks in a user's mouth but not exposed to a toothbrush while brushing, particles and/or bacteria can accumulate in these portions (e.g., lumen of the sheath). By including the apertures in the sheath, portions of the sheath (e.g., inner surfaces) may be accessed for cleaning by brush, water (e.g., soaking, flushing and/or rinsing manually and/or using a device such as a water pick). User hygiene may thus be improved by facilitate cleaning.

The sheath 40 may include a plurality of apertures. The apertures may be any appropriate shape and/or size. The apertures may be disposed as appropriate along a length of the sheath. For example, the sheath may include one or more approximately horizontal apertures 43 and one or more slanted apertures 44. As illustrated, the sheath may include two horizontal apertures 43 and a tongue 45 disposed between the horizontal apertures. The horizontal apertures may join to allow the tongue to extend from the sheath at a first end and terminate at a second end 46 that is not coupled to the sheath (e.g., free end). The tongue may be deformable.

At least a portion of the connector may be coupled to the second bite plate via the sheath. For example, a second arm of the connector may be disposed at least partially in the sheath to couple the second bite plate to the connector and/or first bite plate (e.g., via the connector). The second arm may be capable of moving in the direction of (e.g., sliding along) an axis approximately parallel to the teeth on which the bite plate is disposed and/or approximately parallel to the facial side of the second bite plate. To inhibit the second arm from releasing from the sheath (e.g., pulling the arm of the connector out of the sheath while the user moves the user's mouth) the tongue may be deformed (e.g., bent towards the facial surface of the teeth) to inhibit the second arm from releasing from the sheath. The tongue may be deformed to inhibit the second arm from releasing from the cavity of the sheath while allowing the second arm to move (e.g., slide) along at least a portion of the length of the sheath. For example, the second arm may include a stop 55. The stop may be a member (e.g., with a greater cross-sectional size than the second arm) coupled to the connector and/or may be a portion of the connector that has a greater cross-sectional size (e.g., diameter of a wire) than the second arm. Thus, by decreasing the cross-sectional size of the lumen of the sheath proximate the deformed tongue, the arm of the connector may be inhibited from uncoupling from the cavity of the sheath while movement (e.g., sliding) of the second arm in the sheath may be allowed.

The sheath 40 may be coupled to the second bite plate 20. For example, the sheath 40 may include one or more attachment legs extending from the sheath. One or more attachment legs may be disposed proximate each end of the sheath, in some implementations. Prior to curing the material of the bite plate, legs of the sheath may be disposed in the material of the bite plate. When the material is cured, the legs may be secured to the bite plate. In some implementations, the sheath may be coupled to the second bite plate in any other appropriate manner (e.g., bonding, gluing, embedding, inserting legs into the cured material, etc.).

Figure 16:
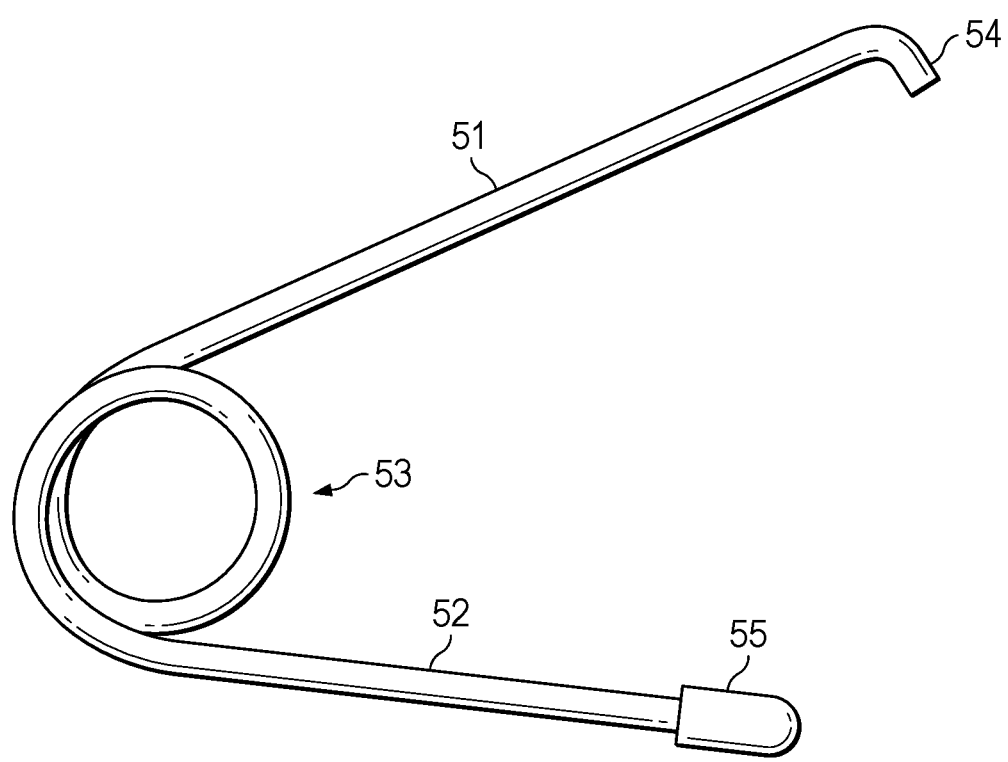
FIG. 16 illustrates an implementation of an example connector.
Figure 17A:
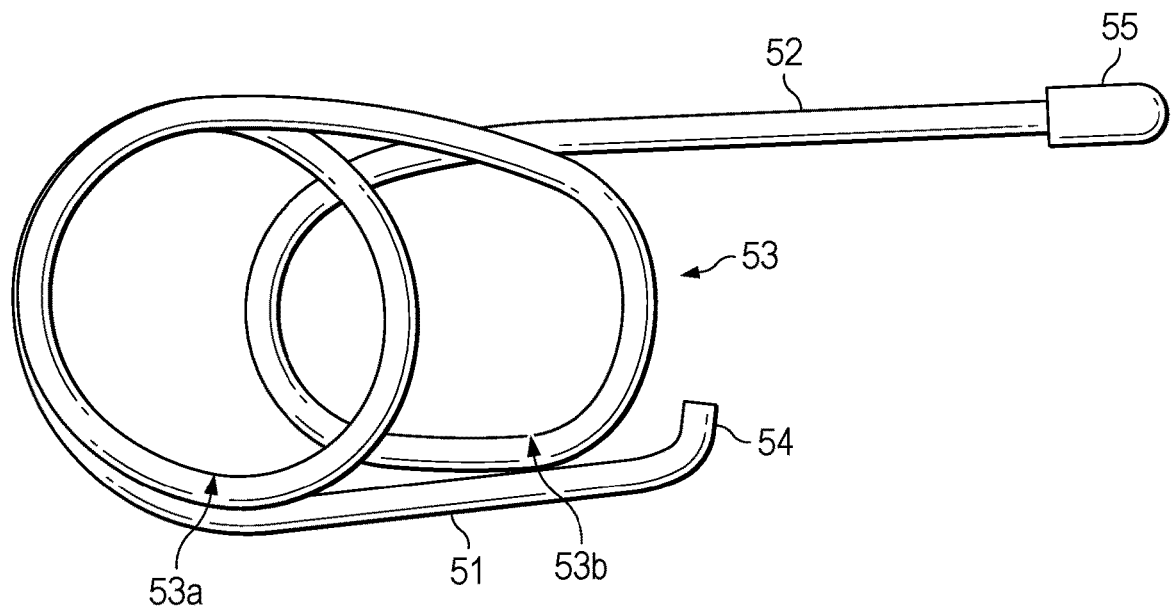
FIG. 17A illustrates a first side view of an implementation of an example connector.
Figure 17B:
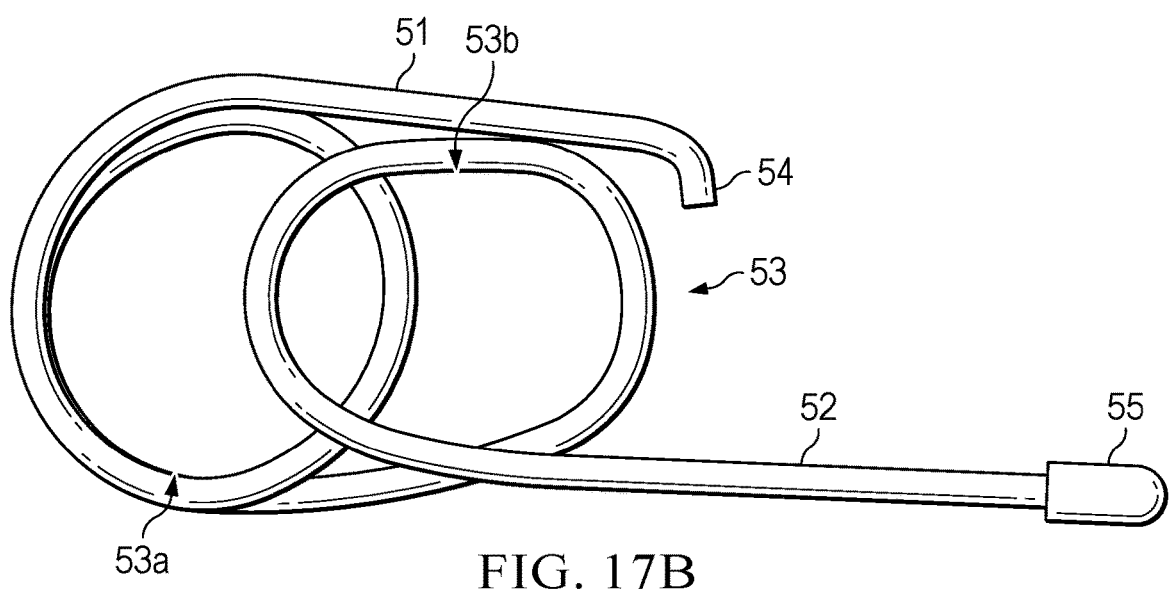
FIG. 17B illustrates a second side view of an implementation of an example connector

The dental appliance 1 may include a connector 50. FIGS. 16-17B illustrate implementations of example connectors. The connector may couple the adjustment member and the sheath of the dental appliance. The connector may be at least partially flexible. For example, while the connector may allow flexibility along a first axis 2 (e.g., side to side movement such movement along a coronal plane) and a second axis 3 (e.g., up and down movement) the connector may restrict movement along a third axis 4 (e.g., movement along an anterior posterior plane). The connector may restrict movement and/or flexibility in along a third axis to allow the connector rigidity sufficient to cause the force exerted on the connector from coupling with a protrusion on the adjustment member to be at least partially transferred to the sheath and thus the second bite plate (e.g., to move the mandible forward for example along axis 2). If the connector is flexible along the third axis, the connector would bend rather than transferring the force to move the mandible forward. The connector may include an initial position and may be flexible to be bent away from the initial position of the connector.

In various implementations, the connector may be configured to return to the initial position (e.g., when a force that causes a the connector to be bent is removed, such after yawning or talking or drinking when the mouth relaxes). The connector may have the capability to return to an initial position by use of a spring mechanism (that allows the movement of the connector while the arm resist deformation) and/or by use of a material that returns to predetermined shape (e.g., elastically deformable material, shape memory materials, etc.).

The connector may include any appropriate material. The connector may include stainless steel. The stainless steel may allow flexibility of the connector via the spring mechanism and/or may allow at least partial transfer of exertive forces from the coupling of the connector and the adjustment member to the sheath (e.g., and the mandible via the second bite plate). For example, the connector may include a shape memory alloy. A shape memory alloy, such as a Titanium Molybdenum Alloy, Nickel Titanium Alloy, may return to an original shape when held above a transition temperature for the alloy. For example, the connector may include a wire that is looped to form a spring mechanism and includes two arms. The transition temperature for the shape memory alloy may be below body temperature (e.g., range of temperatures in a user's mouth). When the connector is in a user's mouth, the user may be able to flex the connector due to the flexible nature of the alloy above the transition temperature. However, when the temperature is above transition temperature for the alloy of the wire, the wire connector will also attempt to return to the wire's original shape and orientation. Thus, a predetermined orientation with respect to the other components of the dental appliance may be maintained while allowing a user flexibility. By allowing the flexibility of the shape memory alloy, user comfort may be increased (e.g., since the user may be able to open and close the user's mouth, talk, eat, drink, etc. without substantially impacting the orientation of the connector during sleep)

The connector 50 may couple with the adjustment member 30 and the sheath 40 of the dental appliance and thus couple the first bite plate 10 and the second bite plate 20 together, as illustrated. The connector 50 may include at least two arms 51, 52 extending from a spring portion (e.g., spring mechanism) 53. The arms may have any appropriate size and/or shape. As illustrated, the arms may be formed from a wire and/or set of wires.

Figure 18A:
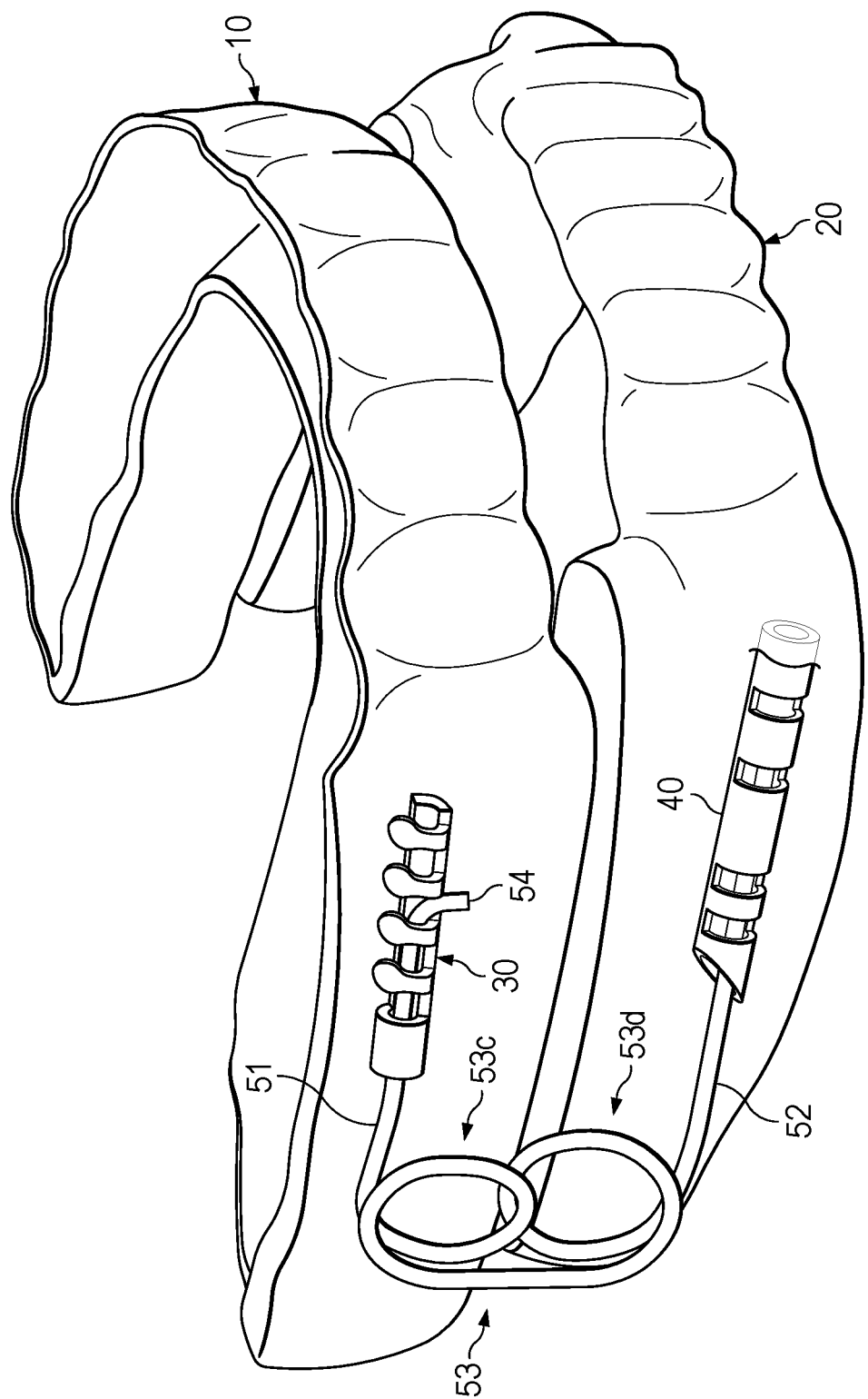
FIG. 18A illustrates a first side view of an implementation dental appliance.
Figure 18B:
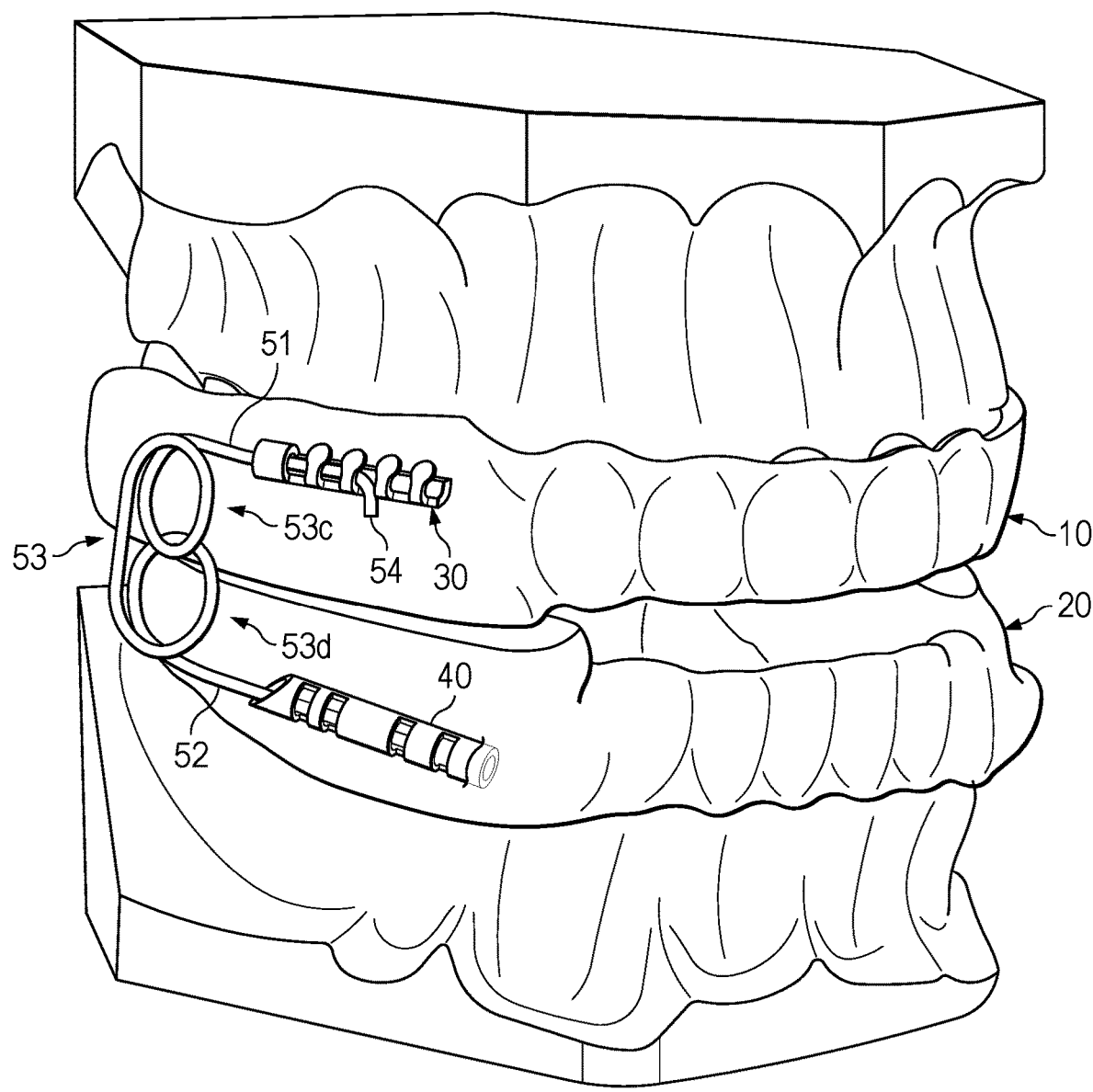
FIG. 18B illustrates a first side view of the implementation of the dental appliance illustrated in FIG. 18A, in use.

The spring portion (e.g., spring mechanism) 53 may include any appropriate spring mechanism such as a set of one or more loops (e.g., one or more helical loops, one or more concentric loops, one or more overlapping loops, etc.) or other elastic object (e.g., elastic bands coupled to ends of arms, etc.). As illustrated in FIG. 16, the spring mechanism 53 may include a loop. As illustrated in FIGS. 17A and 17B, the spring mechanism 53 may include more than one loop. As illustrated, the spring portion 53 may include a first loop 53a and a second loop 53b. The first loop 53a may be disposed closer to the posterior end of the users mouth (e.g., proximate the esophagus) than the second loop 53b (e.g., such that the second loop 53b is closer to the anterior end of the user's mouth than the first loop 53a). The first and the second loops may or may not overlap. As illustrated in FIGS. 18A and 18B, the spring mechanism may include more than one loop. As illustrated, the second loop 53d may be disposed closer to the mandible than the first loop 53c. The first loop and the second loop may or may not overlap.

The size and/or shape of a loop may be customized (e.g., based on user information). A dental professional may receive the connector unlooped and create the loop(s) in the connector to fit the user's mouth and preferences (e.g., for flexibility). In some implementations, the size and/or shape of loop(s) of the connector may be provided to the dental professional in a predetermined shape (e.g., looped and/or straight) the dental professional may or may not adjust the predetermined shape, as appropriate. The size and/or shape of a loop may be similar and/or dissimilar to other loop(s) in the connector. A single wire (e.g., or set of wires) may be bent in a single or multi-loop configuration to form the spring mechanism. As illustrated in FIGS. 17A and 18A, in some implementations, when more than one loop is utilized for form the spring mechanism, one or more of the loops may overlap, partially overlap, and/or be off-set. Off-setting the loops may increase flexibility by decreasing the amount of force a user applies to generate lateral and/or aperture movement in the user's mouth. In some implementations, the loops may or may not extend substantially beyond one or more of the arms of the connector (e.g., the one or more of the loops may reside approximately between the first arm and the second arm). In some implementations, at least a first portion of one or more loops may be proximate the first arm and/or at least a second portion of one or more of the loops may be proximate the second arm.

The spring portion (e.g., spring mechanism) may provide flexibility to the connector and induce return to an initial position. The spring mechanism may increase user comfort while maintaining an adjustment. For example, user comfort while wearing the dental appliance may increase (e.g., when compared with other commercially available devices) since the loop(s) of the spring mechanism allow movement laterally and/or allow a user to open and/or close the user's own mouth (e.g., aperture movements). Thus, the user may talk, drink, eat, stretch the user mouth, and/or otherwise move the mandible laterally and longitudinally. Since the spring mechanism (e.g., loop(s)) returns to the adjustment position after the user releases a force exerted to move (e.g., laterally and/or open/close), the adjustment may be maintained in the device and user comfort may be increased since snoring may decrease and/or airway size may increase. By allowing these movements a user may not feel "locked" into the adjustment position, which may increase user satisfaction and/or compliance with wearing regimens.

In some implementations, the spring portion of the dental appliance may require a predetermined force to cause the mandible of a user to move (e.g., while the user is wearing the dental appliance). The user may exert this force while talking, yawning, drinking, and/or through a variety of other natural and/or unnatural movements. When exerting this force, the user may move the mandible laterally and longitudinally, but the user may be inhibited from substantially moving the mandible from front (e.g., proximate the anterior of the mouth) to back (e.g., proximate the posterior of the mouth) by the spring portion. For example, the user may be inhibited from substantially moving the mandible along axis 2 (e.g., illustrated in FIG. 2), in some implementations. When the force is removed (e.g., the mouth is relaxed, the user is finished with an activity such as talking, drinking, etc.), the spring causes the mandible to return to the position in which it was previously disposed (e.g., mandible extending forward due to the dental appliance). Thus, for example, a user may dispose the dental appliance in the user's mouth prior to bed and continue with normal activities such as talking and drinking since the dental appliance allows lateral and longitudinal movement. Then, when the user falls asleep and/or is relaxed, the dental appliance will exert a force on the mandible to position the mandible in a predetermined position (e.g., in which the mandible is extended forward when compared with the mandible's usual position without the dental appliance).

As illustrated each arm may include a first end coupled to the spring mechanism and a second opposing end. The second end of the first arm 51 may be coupled to the adjustment member 30. The first arm may include a coupling member to couple with the protrusions of the adjustment member. For example, a lock (e.g., hook(s)) 54 may be disposed proximate the second end of the first arm to couple with one or more of the protrusions of the adjustment member. A lock (e.g., hook) may be, for example, a curved, angular, and/or indented portion of the first arm that holds or catches a protrusion of the adjustment member. The lock may be a bend in the wire of the connector. The bend may curve in the opposite direction as the curvature of the protrusions in which the arm is disposed (e.g., the protrusions may curve towards the spine of the attachment member and the lock may curve away from the spine of the attachment member).

As illustrated, the protrusions of the adjustment member may be curved such that a cavity resides between the spine of the adjustment member and protrusion(s) on the facial side of the adjustment member. The first arm may be disposed at least partially in the cavity of the adjustment member. A protrusion may be selected for coupling with the coupling member (e.g., hook) of the first arm of the connector based on the desired adjustment of the mandible (e.g., in a direction along axis 2). For example, the hook of the connector may couple with a first protrusion (e.g., by disposing at least a portion of the coupling member, such as a hook, in the gap between two protrusions and contacting at least one of the protrusions; hook onto a protrusion, etc.) closer to the anterior end of the first bite plate (e.g., in relation to at least one other protrusion) to achieve a first position of the mandible. The hook of the connector may couple with a second protrusion farther from the anterior end of the first bite plate than the first protrusion to achieve a second position of the mandible, where the second position does not extend the mandible as far (e.g., in relation to the maxilla) as the first position.

In various implementations, the dental appliance may be capable of being positioned in more than one position correlated to displacement of the mandible from its initial position (e.g., position when not wearing the dental appliance). The dental appliance may be disposed in a position by coupling the coupling member (e.g., hook) of the connector with a protrusion of the attachment member. As the coupling member of the connector is coupled to gaps (e.g., between protrusions) closer to an anterior side of the user, the mandible is moved further forwards. FIG. 10 illustrates an implementation of a dental appliance in a first position, FIG. 11 illustrates an implementation of a dental appliance in a third position, and FIG. 12 illustrates an implementation of a dental appliance in a second or maximum displacement position (e.g., proximate the protrusion closest to the anterior side of the user and/or farthest away from the posterior end of the user and/or throat of a user). A dental professional and/or user may adjust the position of the dental appliance to decrease and/or inhibit snoring. In some implementations, user comfort may increase as the amount of displacement of the mandible decreases. Thus, a user may first attempt to decrease and/or inhibit snoring using a first position and/or other positions less than the second position prior to adjusting the dental appliance to the second position. Since the connector can be coupled and/or uncoupled, different levels of mandible adjustment may be possible using the same dental appliance. User satisfaction and/or dental professional satisfaction may be increased since costs may be decreased (e.g., costs special tools may not be utilized and/or new dental appliances may not need to be purchased, etc.), a less severe adjustment may be attempted for relief without concerns of expense to adjust the dental appliance.

The second arm of the connector may be at least partially disposed in a cavity of the sheath, during use. The second arm may include a stop 55 to couple the second arm of the connector to the sheath and/or second bite plate. The stop 55 may be any appropriate size and/or shape. For example, the stop may have a greater diameter than the diameter of the second arm. The stop may be disposed proximate the second end of the second arm, in some implementations. As illustrated, the stop may be disposed in a cavity of the sheath. To couple the second arm to the sheath and/or second bite plate, the tongue may be deformed, in some implementations. For example, since the tongue of the sheath is deformable, once the stop is disposed in the cavity of the sheath past the tongue (e.g., closer to the anterior end of the bite plate than the tongue) the tongue may be depressed to deform the tongue and decrease the diameter of the cavity proximate the tongue. This deformation may inhibit the stop of the second arm from passing through the reduced diameter cavity created by the deformed tongue and thus couple the second arm and the tongue.

The dental appliance may be inserted into a user's mouth pre-coupled, in some implementations. A dental professional may select bite plates that are capable of coupling with a user's upper and lower teeth. For example, a dental professional may create a mold of a user's teeth to create bite plates that are adapted to couple with the users teeth (e.g., to allow frictional retention of the bite plates and/or easy removal by a user). During creation of the bite plates, the adjustment member may be coupled to the first bite plate and the sheath may be coupled to the second bite plate (e.g., by positioning the adjustment member and/or sheath in the matrix to form the bite plate prior to curing the bite plates and/or via other coupling methods). In some implementations, a dental professional may select a bite plate from a set of bite plates of different configurations and/or sizes. The adjustment member and/or sheath may be coupled to the selected bite plates (e.g., via adhesive, bonding agent, etc.).

The bite plates may be disposed in the user's mouth. A first arm of the connector may be coupled to a protrusion of the adjustment member and a second arm of the connector may be disposed in the sheath. The position of the first bite plate to the second bite plate may be adjusted by coupling the hook of the first arm to a different protrusion (e.g., to position the mandible more or less forward), in some implementations. Thus, a dental professional may create the appropriate increase in airway by adjusting the coupling of the connector to the adjustment member. In some implementations, the second arm of the connector may or may not be coupled to the sheath. The second arm of the connector may be coupled to the sheath to inhibit the second arm from being drawn out of the sheath (e.g., during removal, placement, and/or movement within the mouth).

In various implementations, a dental appliance may include a sheath and an adjustment member coupled via a connector. The dental appliance may or may not include one or more bite plates. For example, an adjustment member and/or sheath may be coupled to orthodontic bases, such as the bases described in U.S. patent application Ser. No. 12/484,082 (entitled "Orthodontic Devices"), which is incorporated by reference herein to the extent that it does not conflict disclosed implementations. For example, the sheath described in U.S. patent application Ser. No. 12/484,082 may be utilized instead of the described sheath and/or the described sheath may replace the sheath of U.S. application Ser. No. 12/484,082. In some implementations, the adjustment member and/or sheath may be coupled to one or more orthodontic brackets coupled to a user's teeth. By utilizing existing orthodontic appliances in a user's mouth, the dental appliance may be used in a plurality of different types of users. For example, a user with existing dental appliances may not be able to use a dental appliance with a bite plate. Thus, the ability to couple the adjustment member and/or sheath to the existing dental appliances (e.g., bases, brackets, etc.) may allow use of the described device in users that otherwise may not be able to use the described dental appliances and/or reduce costs for users with existing dental appliances.

In various implementations, a dental appliance may include a first bite plate, a second bite plate, and at least one connector that couples the first bite plate to the second bite plate. The first bite plate may include an inner surface adapted to receive one or more upper teeth and an outer surface. The first bite plate may include at least one adjustment member disposed at least partially on an outer surface of the first bite plate. An adjustment member may include an opening disposed at least partially through the adjustment member and more than one lock position. A second bite plate may include an inner surface adapted to receive one or more lower teeth and an outer surface. The second bite plate may include at least one sheath disposed at least partially on an outer surface of the second bite plate. The connector may include a first arm, a second arm, and a spring portion. The first arm may include a lock. At least a portion of the first arm may be received in the opening of an adjustment member. The lock may retain the first arm in one of the lock positions of the adjustment member. The dental appliance may anteriorly move a position of a mandible of a user when the lock of the first arm is retained in at least one of the positions of an adjustment member. The second arm may be received in one of the sheaths (e.g., an opening disposed through a length of the sheath). The spring portion may be disposed between the first arm and the second arm. A connector may couple the first bite plate and the second bite plate such that lateral and longitudinal movement is allowed by the spring of each of the connectors.

Implementations may include one or more of the following features. The dental appliance may include attachment member on a first side and an attachment member on a second side of the first bite plate. The dental appliance may include a sheath on a first side and a sheath on a second opposing side of the second bite plate. An attachment member may be positioned on a first bite plate and a sheath may be disposed on a second bite plate such that a first arm of the connector may a disposed in the attachment member and the second arm of the connector may be disposed in the sheath. The lock may include a bent portion of the first arm of the connector. The bent portion may include a curvature such that the lock may be retained in a lock position of the adjustment member. At least one of the adjustment members may be disposed on a facial surface of the first bite plate. At least one of the sheaths may be disposed on a facial surface of the second bite plate. The dental appliance may include two adjustment members and two sheaths. The adjustment members may be disposed on opposing sides of the first bite plate. The sheaths may be disposed on opposing sides of the second bite plate. The spring portion of each of the connectors may include at least one loop. In some implementations, the spring portion of each of the connectors includes two loops. One of the loops may be disposed closer to the first bite place than the other loop. One of the loops may be disposed closer to the anterior end of the mouth of the user than the other loop. The loops may or may not overlap. The inner surface of the first bite plate may have an approximately corresponding shape to one or more of the upper teeth disposed in the first bite plate such that the first bite plate is frictionally retained in a palate of a user. The inner surface of the second bite plate may have an approximately corresponding shape to one or more of the lower teeth disposed in the second bite plate such that the second bite plate is frictionally retained in the palate of the user. The inner surface of the first bite plate may receive one or more of the upper teeth. The inner surface of the second bite plate may receive one or more of the lower teeth. The inner surface of the first bite plate and/or the inner surface of the second bite plate may fit a predetermined range of users. The bite plate (e.g., first bite plate and/or second bite plate) may include a lingual side and a facial side extending from an occlusal side of the bite plate. A bite plate may include a lingual side extending from an occlusal side of the bite plate, in some implementations. A bite plate may include a palate portion. The palate portion may be disposed proximate and/or may contact at least a portion of a palate of a user. A palate portion may have a curvature approximately the same as a palate of a user. An adjustment member may include a spine and a plurality of protrusions. The plurality of protrusions may be disposed along the spine such that gaps are disposed between adjacent protrusions. The protrusions may be disposed on a first side of the spine and/or a second opposing side of the spine of the adjustment member. In a lock position of the adjustment member, one of the locks of one of the first arms may be disposed at least partially in one of the gaps. In some implementations, at least a portion of an attachment member may be disposed in the first bite plate. For example, protrusions on one side of the spine and/or at least a portion of the spine may be disposed in the bite plate (e.g., such that protrusions on the opposing side of the spine extend from the bite plate). The protrusion(s) may be curved towards the inner surface of the first bite plate.

In various implementations, a dental appliance may include at least one adjustment member, coupleable to one or more upper teeth of a user, and at least one connector. An adjustment member may include a spine, a plurality of protrusions, and gaps. The plurality of protrusions may extend from at least one side of the spine. One or more of the plurality of protrusions may be curved towards the spine. Gaps may be disposed between one or more of the adjacent protrusions of the plurality of protrusions. A gap may correspond to a lock position (e.g., when a lock is disposed at least partially in a gap, the lock may be retained such that the dental appliance is in a lock position of the attachment member). A connector may include at least one wire. A wire may include a first arm, a second arm and a spring section. The first arm may extend from a spring section of the wire and/or may include a lock. The second arm second arm may extend from the spring section of the wire. The spring section may include an upper loop and a lower loop. The upper loop may be disposed at least partially above the lower loop. The at least one connector may be coupled (e.g., indirectly or directly) to one or more of the upper teeth via the at least one adjustment member and may be coupled (e.g., indirectly or directly) to one or more lower teeth of the user. The dental appliance may be adapted to adjust a mandible of a user to a position in which the mandible is disposed more anteriorly than when the dental appliance is not disposed in a mouth of the user.

Implementations may include one or more of the following features. In some implementations, at least a portion of the protrusions on a first side of the spine may be curved towards the spine and at least a portion of the protrusions on a second side of the spine may be curved away from the spine. In some implementations, one or more of the protrusions that curve away from the spine may be coupled to and/or disposed in a first bite plate, orthodontic base(s), and/or orthodontic bracket(s). The wire may or may not be uniform thickness. The wire may be a single wire, in some implementations. The wire may be flexible to allow a user to exert a force (e.g., by movement of the mandible) against the spring portion to move the user's mandible laterally and/or longitudinally. The spring portion of the wire may be configured to return the mandible to a predetermined position (e.g., determined by the lock position of the dental appliance). The upper loop and the lower loop may at least partially overlap. The lock may be a portion of the wire that is curved in an approximately opposite direction as one or more of the curved protrusions such that the lock is retained in one or more of the of the gaps. The attachment member may be indirectly coupled to the upper teeth. A sheath may be coupled to one or more of the lower teeth of the user. The second arm of the wire may be adapted to be slidably disposed at least partially in one of the sheaths. A sheath may be coupled to one or more of the lower teeth of the user via an orthodontic base and/or an orthodontic bracket. The attachment member may be coupled to an orthodontic base and/or an orthodontic bracket to couple to one or more of the upper teeth.

In various implementations, snoring may be treated using the dental appliance. The dental appliance may be disposed in a mouth of a user such that a mandible of the user is moved forward to a first position. The first position may move the mandible closer to the anterior side of the user than the position (e.g., initial position) of the mandible when the dental appliance is not disposed in the mouth of the user. The user may be allowed to move the user's mandible laterally and longitudinally when the user applies a force to the mandible (e.g., when the user opens or closes the user's mouth, when the user talks, drinks, and/or eats, etc.). The mandible may be allowed to return to a position where the mandible is extended forward to the first position when the force is removed (e.g., via the spring portion of the connector which exerts a force on the resting and/or relaxed mandible). The dental appliance may include a first bite plate, a second bite plate and at least one connector. The first bite plate may include an inner surface adapted to receive one or more upper teeth and an outer surface. The first bite plate may include two adjustment members disposed at least partially on an outer surface of the first bite plate. One of the adjustment members may be disposed on a first side of the bite plate, and the other adjustment member may be disposed on the opposing second side of the first bite plate. An adjustment member may include an opening disposed at least partially through the adjustment member and more than one lock position. A lock position may include a gap in the adjustment member. A second bite plate may include an inner surface adapted to receive one or more lower teeth and an outer surface. The second bite plate may include two sheaths disposed at least partially on an outer surface of the second bite plate. One of the sheaths may be disposed on a first side of the second bite plate, and the other sheath may be disposed on a second opposing side of the second bite plate. The dental appliance may include two connectors. For example, the connector may be disposed proximate one or both sides of the first bite plate and the second bite plate. A connector may include a first arm, a second arm, and a spring portion disposed between the first arm and the second arm. The first arm and the second arm may extend from the spring portion. A first arm may include a lock. At least a portion of the first arm may be received in the opening of one of the adjustment members. The lock may be adapted to retain first arm in at least one of the gaps of the adjustment members. The dental appliance may be adapted to anteriorly move a position of a mandible of a user when the lock of the first arm is retained in one of the positions of one of the adjustment member. At least a portion of the second arm may be received a sheath (e.g., in an opening extending along a length of the sheath). A connector may couple the first bite plate and the second bite plate such that lateral and longitudinal movement is allowed by the spring of each of the connectors.

Implementations may include one or more of the following features. A position of the mandible of the user may be adjusted from the first position to a second position. The second position may draw the mandible closer to the anterior side of the mouth or farther from the anterior side of the mouth. To widen the airway, the mandible may be drawn closer to the anterior side of the mouth, in some implementations. A dental professional may adjust which the lock position the lock of the first arm is in based on whether snoring continues. For example, the lock position that is the least forward extended mandible that inhibits snoring may be selected for the comfort of the user. In some implementations, adjusting a position may include unlocking the locks on each of the first arms from a first gap of each of the attachment member; and anteriorly moving the first arm to retain each of the locks in a second gap that is more anteriorly positioned than the first gap.

In some implementations, breathing airway in a user may be increased using the dental appliance. A breathing airway may be increased in the user when the dental appliance is disposed in the mouth of a user (e.g., and the lock position extends the mandible forward/more anteriorly than the mandible position without the dental appliance.)

In some implementations, the dental appliance may be produce using custom bite plates (e.g., bite plates molded to a user's palate and/or teeth) and/or using bite plates adapted to fit a predetermined range of user's mouths. Custom bite plates may provide room for existing orthodontia (e.g., orthodontic bases, brackets, wires, buttons, etc.) and/or other dental devices (e.g., braces). In some implementations, the orthodontic brackets and/or bases may be used in place of one or more of the bite plates with attachment members and/or sheaths. For example, a user may have existing orthodontic devices in the user's mouth, such as orthodontic brackets and/or orthodontic bases. The attachment member and/or sheath may be coupled to the existing orthodontic devices such that the described dental appliance may be used in such patients (e.g., as opposed to creating bite plates that fit around existing orthodontia).

In various implementations, the forward adjustment of the mandible (e.g., when compared with a position of the mandible when the dental appliance is not in use) may increase a user's airway and decrease snoring and/or improve a user's health (e.g., due to lack of sleep, lack of oxygen when sleeping, internal vibration caused by snoring, etc.). The forward adjustment of the mandible may be temporary such that when the described dental appliance is removed from a user's mouth, the user's mandible returns to a position that is approximately the same as the initial position (e.g., position of a user's mandible prior to insertion of the dental appliance.

The described dental device may be less expensive, more comfortable, and/or more hygienic than other snoring aids. For example, surgery is costly, requires healing time, and may not achieve a reduction in snoring. The described devices include simple parts and may thus have lower production costs (e.g., when compared to devices with complex spring pins and other components, etc.). The described device may not include a center screw to hold the mandible open and/or forward, and thus may be more comfortable since it does not interfere with tongue position. The described device may be more comfortable than other devices since the described devices may allow lateral (e.g., approximately parallel to the coronal plane, approximately parallel to axis 3), longitudinal (e.g., parallel to a sagittal plane, approximately parallel to axis 4, approximately normal to axis 2 and 3), and anterior-posterior movement (e.g., in a direction of axis 2) while other devices may restrict movement. Allowing movement while the described device is being worn may allow a user to talk, drink, and/or eat, and thus increase user enjoyment of the device. In some implementations, hygiene may be improved since the dental appliance may include features that facilitate cleaning (e.g., apertures in sheath, openings above and/or between protrusions of attachment member, etc.).

In various implementations, the described dental appliance may be easily adjustable, which may reduce costs and increase user comfort. For example, if an adjustment is too severe (e.g., the mandible is pushed to far forward for user comfort), the protrusion to which the connector is coupled may be adjusted. In some implementations, if snoring is not reduced, the mandible may be moved farther forward (e.g., by coupling the connector to a protrusion closer to the anterior end than the currently coupled protrusion). In some implementations, the mandible position may be gradually increased forward to increase user comfort (e.g., allow user adjustment time) and/or to allow the smallest adjustment to the mandible position to be utilized (e.g., which may increase user comfort).

In various implementations, the described device may have a lower facial side profile (e.g., when compared with other snoring aids), which may increase user comfort.

In various implementations, user comfort may be increased when a user utilizes the device (e.g., when compared with other snoring aids). For example, by allowing movement in the first and/or second planes when the dental appliance is worn, a user's natural sleep movements may be maintained. In some implementations, a user that grinds teeth during or proximate sleep times may be allowed to continue this grinding movement while wearing the dental appliance due to the dental appliance's flexibility (e.g., via the connector). Thus, a user's sleep may not be disrupted by restricting movement, such as grinding, and a user's comfort may be increased. The occlusal surface of the bite plate(s) may inhibit damage to the enamel due to grinding, in some implementations.

Described processes may be implemented by various systems, such the described systems. In addition, various operations may be added, deleted, and/or modified. In some implementations, a described process may be performed in combination with other described processes or portions thereof.

Although various implementations describe the attachment member and the sheath of the dental appliance being coupled to the mouths via bite plates, the attachment member and/or sheath may be coupled to the mouths via other dental coupling members. For example, the attachment member and/or sheath may be coupled to orthodontic bases to couple to one or more teeth or portions thereof in the mouth. The attachment member and/or sheath may be coupled to orthodontic brackets to couple to one or more teeth or portions thereof in the mouth. The attachment member and the sheath may or may not couple (e.g., removably) to the mouth of the user using the similar dental coupling members. For example, the dental appliance may utilize a first bite plate with an attachment member and a sheath coupled to an orthodontic base and/or bracket (e.g., thus the sheath may remain in the mouth of the user when the dental appliance is removed). The second arm of a connector may removably slide into the sheath and the first arm may lock into a gap (e.g., to establish a lock position). In some implementations, the second arm of the connector may not include a stop to facilitate removability when using a sheath coupled to an orthodontic base and/or bracket. In some implementations, an attachment member may be coupled to an orthodontic base and/or bracket (e.g., such that the attachment member remains in the mouth while the rest of the dental appliance is removed) and a second bite plate may be coupled to the sheath. The first arm of a connector may be disposed in the attachment member and locked via the lock into a lock position to extend the mandible forward.

Although various implementations describe the attachment member and the sheath of the dental appliance being coupled to the mouths via bite plates, the attachment member and/or sheath may be coupled to the mouths via other dental coupling members. These implementations may include one or more of the features described in connection with the bite plate implementations.

Although various figures include dimensions (e.g., mm), other implementations may include different dimensions including different ratios between components. For example, the gap between protrusions of an attachment member may increase or decrease even if the size of the protrusion remains the same. The dimensions and/or ratios of dimensions in one or more of the components may be fixed and/or variable. In some implementations, the dimensions may be customized based on the user.

Although directional terms have been utilized, the directional terms have been relative to the device and/or user, as specified rather than general orientation terms.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a sheath" includes a combination of two or more sheaths and reference to "a memory metal" includes different types and/or combinations of memory metals.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A dental appliance comprising:
   at least one connector, wherein each connector of the at least one connector comprises:
      a first arm having an end comprising a hook;
      a second arm having an end comprising a stop, wherein the stop of the second arm comprises a diameter greater than a diameter of the second arm; and
      a spring portion disposed between the first arm and the second arm;
   a first bite plate, wherein the first bite plate comprises:
      an inner surface adapted to receive one or more upper teeth;
      an outer surface; and
      at least one adjustment member disposed at least partially on the outer surface of the first bite plate, wherein each adjustment member comprises:
         one or more protrusions,
            wherein each protrusion comprises a first end coupled to a spine of the adjustment member and a second end;
            wherein a first portion of each protrusion of the one or more protrusions that is proximate the first end extends away from the outer surface of the first bite plate,
            and wherein a second portion of each of the protrusions curves towards the first bite plate, wherein the second portion is disposed closer to the second end than the first portion;
         a longitudinal opening disposed parallel to the spine of the adjustment member and disposed along at least a portion of a length of the adjustment member and disposed between the one or more protrusions and the outer surface of the first bite plate, wherein the longitudinal opening is capable of receiving the end of the first arm of the at least one connector; and
         more than one gap, wherein each gap of the more than one gap is disposed between adjacent protrusions of the one or more protrusions, and wherein each gap of the more than one gap comprises:
            a lock position of the adjustment member;
            and wherein each gap of the more than one gap is capable of coupling with the hook of the first arm to occupy the lock position of the gap such that at least a portion of the hook is disposed in the gap and extends at least partially beyond the adjustment member to be disposed proximate the outer surface of the first bite plate;
   a second bite plate, wherein the second bite plate comprises:
      an inner surface adapted to receive one or more lower teeth;
      an outer surface;
      at least one longitudinal sheath disposed at least partially on the outer surface of the second bite plate, wherein the at least one longitudinal sheath is capable of receiving the end of the second arm, wherein a portion of the at least one longitudinal sheath comprises a deformable tongue, wherein the deformable tongue is capable of deforming to reduce the inner cross-section of said portion of the at least one longitudinal sheath to thereby inhibit the second arm of the at least one connector from exiting the at least one longitudinal sheath via the stop of the second arm once deformed;
   wherein the dental appliance is adapted to anteriorly move a position of a mandible of a user when the hook of the first arm is retained in at least one of the gaps of one of the adjustment member;
   wherein each of the connectors is adapted to couple the first bite plate and the second bite plate such that movement in a lateral and a longitudinal direction is allowed by the spring of each of the connectors;
   wherein when the dental appliance is in use, the dental appliance allows the user to move the mandible in a laterally and longitudinally direction when the user applies a force to the mandible; and
   wherein the dental appliance returns to a position where the mandible is extended forward when the force is removed.

2. The dental appliance of claim 1 wherein at least one of the adjustment members is disposed on a facial surface of the first bite plate, and wherein at least one of the sheaths is disposed on a facial surface of the second bite plate.

3. The dental appliance of claim 1 wherein the dental appliance comprises two adjustment members and two sheaths, wherein the two attachment members are disposed on opposing sides of the first bite plate, and wherein the sheaths are disposed on opposing sides of the second bite plate.

4. The dental appliance of claim 1 wherein the spring portion of each connector of the at least one connector comprises at least one loop.

5. The dental appliance of claim 1 wherein the spring portion of each connector of the at least one connector comprises two loops, wherein one of the loops is disposed closer to the first bite plate than the other loop.

6. The dental appliance of claim 1 wherein the inner surface of the first bite plate is configured to have approximately corresponding shape to the one or more upper teeth disposed in the first bite plate such that the first bite plate is frictionally retained in a palate of the user; and wherein the inner surface of the second bite plate is configured to have approximately corresponding shape to receive the one or more lower teeth disposed in the second bite plate such that the second bite plate is frictionally retained in the palate of the user.

7. The dental appliance of claim 1 wherein the inner surface of the first bite plate is configured to fit a predetermined range of users; and wherein the inner surface of the second bite plate is configured to fit the predetermined range of users.

8. The dental appliance of claim 1 wherein the first bite plate includes a lingual side and a facial side extending from an occlusal side of the first bite plate; and
wherein the second bite plate includes a lingual side and a facial side extending from an occlusal side of the second bite plate.

9. The dental appliance of claim 1 wherein the first bite plate includes a palate portion, and wherein the palate portion is configured to have a curvature approximately the same as a palate of the user.

10. The dental appliance of claim 1 wherein one or more of the protrusions are curved towards the inner surface of the first bite plate.

11. A dental appliance comprising:
at least one connector comprising a wire, wherein the wire comprises:
a first arm extending from a spring section of the wire, wherein the first arm has an end comprising a hook; and
a second arm extending from the spring section of the wire;
wherein the spring section of the wire comprises an upper loop and a lower loop, wherein the upper loop is disposed at least partially above the lower loop, and wherein the first arm extends from the upper loop and the second arm extends from the lower loop in a same direction;
at least one adjustment member coupleable to one or more upper teeth of a user, wherein each adjustment member comprises:
a spine;
one or more protrusions,
wherein each protrusion comprises a first end coupled to the spine of the adjustment member and a second end;
wherein a first portion of each protrusion of the one or more protrusions that is proximate the first end is adapted to extend away from the one or more upper teeth,
and wherein a second portion of each of the protrusions is adapted to curve towards the one or more upper teeth, wherein the second portion is disposed closer to the second end than the first portion;
a longitudinal opening disposed parallel to the spine of the adjustment member and disposed along at least a portion of a length of the adjustment member and adapted to be disposed between the one or more protrusions and the one or more upper teeth, wherein the longitudinal opening is capable of receiving the end of the first arm of the at least one connector;
gaps disposed between one or more of the adjacent protrusions of the plurality of protrusions, wherein each gap corresponds to a lock position, and wherein each gap is capable of coupling with the hook of the first arm to occupy the lock position of the respective gap such that at least a portion of the hook is disposed in the respective gap and extends at least partially beyond the adjustment member;
wherein the at least one connector is adapted to be coupled to one or more of the upper teeth via the at least one adjustment member; and wherein the at least one connector is adapted to be coupled to one or more lower teeth of the user;
and wherein the dental appliance is adapted to adjust a mandible of the user to a position in which the mandible is disposed more anteriorly than when the dental appliance is not disposed in a mouth of the user, and wherein the spring section allows the user to move the mandible in a laterally and longitudinally when the user applies a force to the mandible; wherein the dental appliance returns to a position where the mandible is extended forward when the force is removed.

12. The dental appliance of claim 11 wherein the adjustment member is indirectly configured to be coupled to the upper teeth.

13. The dental appliance of claim 11 further comprising at least one sheath configured to be coupled to one or more of the lower teeth of the user; wherein the second arm of the wire is adapted to be slidably disposed at least partially in one of the sheaths.

14. The dental appliance of claim 13 wherein the at least one sheaths is configured to be coupled to one or more of the lower teeth of the user via at least one of an orthodontic base or orthodontic bracket.

15. The dental appliance of claim 11 wherein the adjustment member is configured to be coupled to at least one of an orthodontic base or an orthodontic bracket configured to be coupled to one or more of the upper teeth.

16. A method of treating snoring comprising:
disposing a dental appliance in a mouth of a user such that a mandible of the user is moved forward to a first position, wherein the first position moves the mandible closer to an anterior side of the user than the position of the mandible when the dental appliance is not disposed in the mouth of the user, wherein the dental appliance comprises:
two connectors, wherein each connector comprises:
a first arm having an end comprising a hook;
a second arm having an end comprising a stop, wherein the stop of the second arm comprises a diameter greater than a diameter of the second arm; and a spring portion disposed between the first arm and the second arm;
a first bite plate, wherein the first bite plate comprises:
an inner surface adapted to receive one or more upper teeth;
an outer surface;
two adjustment members disposed at least partially on the outer surface of the first bite plate, wherein one of the adjustment members is disposed on a first side of the bite plate, and wherein the other adjustment member is disposed on an opposing second side of the first bite plate, and wherein each adjustment member comprises:
one or more protrusions,
wherein each protrusion comprises a first end coupled to a spine of the adjustment member and a second end:
wherein a first portion of each protrusion of the one or more protrusions that is proximate the first end extends away from the outer surface of the first bite plate,
and wherein a second portion of each of the protrusions curves towards the first bite plate, wherein the second portion is disposed closer to the second end than the first portion;
a longitudinal opening disposed parallel to the spine of the adjustment member and disposed along at least a portion of a length of the adjustment member and disposed between the one or more protrusions and the outer surface of the first bite plate, wherein the longitudinal opening is capable of receiving the end of the first arm of each connector; and
more than one gap, wherein each gap of the more than one gap is disposed between adjacent protrusions of the one or more protrusions, and wherein each gap of the more than one gap comprises:
a lock position of the adjustment member;
and wherein each gap of the more than one gap is capable of coupling with the hook of the first arm to occupy the lock position of the gap such that at least a portion of the hook is disposed in the gap and extends at least partially beyond the adjustment member to be disposed proximate the outer surface of the first bite plate; and
a second bite plate, wherein the second bite plate comprises:
an inner surface adapted to receive one or more lower teeth;
an outer surface;
two longitudinal sheaths disposed at least partially on the outer surface of the second bite plate, wherein one of the longitudinal sheaths is disposed on a first side of the second bite plate, and wherein the other longitudinal sheath is disposed on a second opposing side of the second bite plate, wherein each longitudinal sheath is capable of receiving the end of the second arm of one of the two connectors, and wherein a portion of each of the two longitudinal sheaths comprises a deformable tongue, wherein the deformable tongue is capable of deforming to reduce the inner cross-section of said portion of each of the two longitudinal sheaths to thereby inhibit the stop of the second arm from releasing from the one of the longitudinal sheaths once deformed;
wherein the dental appliance is adapted to anteriorly move a position of a mandible of the user when the hook of the first arm is retained in one of the gaps of one of the adjustment members;
wherein each of the connectors is adapted to couple the first bite plate and the second bite plate such that lateral and longitudinal movement is allowed by the spring of each of the connectors;
allowing the user to move the mandible laterally and longitudinally when the user applies a force to the mandible; and
returning to a position where the mandible is extended forward to the first position when the force is removed.

17. The method of claim 16 further comprising adjusting position of the mandible of the user from the first position to a second position, wherein the second position positions the mandible of the user closer to the anterior side of the user than the first position, and wherein adjusting position comprises:
unlocking the hooks on each of the first arms from a first gap of the more than one gaps of each of the attachment members,
anteriorly moving the first arm to retain each of the hooks in a second gap of the more than one gaps of each of the attachment members that is more anteriorly positioned than the first gap.

18. The method of claim 16 wherein a breathing airway is increased in the user when the dental appliance is disposed in the mouth of the user.

* * * * *